(12) United States Patent
Cowan et al.

(10) Patent No.: US 8,838,235 B2
(45) Date of Patent: Sep. 16, 2014

(54) WEARABLE DEFIBRILLATOR SYSTEM COMMUNICATING VIA MOBILE COMMUNICATION DEVICE

(71) Applicant: Physio-Control, Inc., Redmond, WA (US)

(72) Inventors: Kenneth Frederick Cowan, Kirkland, WA (US); Isabelle Banville, Newcastle, WA (US); Robert Reuben Buchanan, Redmond, WA (US); David Peter Finch, Bothell, WA (US); Joseph Leo Sullivan, Kirkland, WA (US); Phillip D. Foshee, Woodinville, WA (US); Laura Marie Gustavson, Redmond, WA (US); Daniel Ralph Piha, Bellevue, WA (US); Carmen Ann Chacon, Vashon, WA (US); Blaine Krusor, Seattle, WA (US); Gary Debardi, Kirkland, WA (US); Richard C. Nova, Seattle, WA (US); Krystyna Szul, Seattle, WA (US); Gregory T. Kavounas, Bellevue, WA (US)

(73) Assignee: Physio-Control. Inc., Redmond, WA (US)

( * ) Notice: Subject to any disclaimer, the term of this patent is extended or adjusted under 35 U.S.C. 154(b) by 0 days.

(21) Appl. No.: 13/959,876

(22) Filed: Aug. 6, 2013

(65) Prior Publication Data
US 2014/0046391 A1 Feb. 13, 2014

Related U.S. Application Data

(60) Provisional application No. 61/682,143, filed on Aug. 10, 2012, provisional application No. 61/706,697, filed on Sep. 27, 2012, provisional application No. 61/768,897, filed on Feb. 25, 2013.

(51) Int. Cl.
| | | |
|---|---|---|
| *A61N 1/00* | (2006.01) |
| *H04W 4/22* | (2009.01) |
| *G06F 19/00* | (2011.01) |
| *A61B 5/00* | (2006.01) |
| *A61N 1/39* | (2006.01) |

(52) U.S. Cl.
CPC .............. *A61N 1/3993* (2013.01); *H04W 4/22* (2013.01); *G06F 19/3418* (2013.01); *A61N 1/3937* (2013.01); *A61B 5/0022* (2013.01)
USPC .......................................................... 607/5

(58) Field of Classification Search
USPC ........................................................... 607/5
See application file for complete search history.

(56) References Cited

U.S. PATENT DOCUMENTS 6,304,780 B1 * 10/2001 Owen et al. ....................... 607/5
6,747,556 B2 6/2004 Medema et al.
(Continued)

FOREIGN PATENT DOCUMENTS

| WO | 9839061 | 9/1998 |
| WO | 2009001361 | 12/2008 |
| WO | 2013096954 | 6/2013 |

OTHER PUBLICATIONS

Lifepak(R) 1000 AED Operator's instructions—reproduced segment.

*Primary Examiner* — George Manuel
(74) *Attorney, Agent, or Firm* — Kavounas Patent Law Office, PLLC.

(57) ABSTRACT

A wearable defibrillation system can establish a local comlink with a mobile communication device, such as a smartphone, tablet-type computer and the like. The mobile communication device can in turn establish a remote comlink with other devices in a network such as the internet. Accordingly, communication tasks relating to the wearable defibrillation system can be performed via the local and the remote comlinks, with or without the participation of the patient, who is wearing the system. The wearer can thus use the familiar interface of a mobile communication device for interacting with his defibrillator system. Moreover, he can do so while keeping on his regular clothes, which could conceal completely the wearable defibrillator system. The patient can thus preserve his dignity and privacy.

39 Claims, 16 Drawing Sheets

(56) References Cited

U.S. PATENT DOCUMENTS

| | | |
|---|---|---|
| 8,086,320 B2 | 12/2011 | Saketkhou |
| 8,099,163 B2 | 1/2012 | Jung et al. |
| 8,140,154 B2 | 3/2012 | Donnelly |
| 8,180,457 B2 | 5/2012 | Matos |
| 8,323,189 B2 | 12/2012 | Tran et al. |
| 8,369,944 B2 | 2/2013 | Macho et al. |
| 2007/0213775 A1 | 9/2007 | Snyder |
| 2009/0005827 A1 | 1/2009 | Weintraub et al. |
| 2009/0076559 A1* | 3/2009 | Libbus et al. .......... 607/6 |
| 2012/0158074 A1 | 6/2012 | Hall |
| 2013/0012151 A1 | 1/2013 | Hankins |
| 2013/0144355 A1 | 6/2013 | Macho et al. |

* cited by examiner

COMMUNICATION ARRANGEMENT

*WEARABLE DEFIBRILLATOR SYSTEM & MOBILE COMMUNICATION DEVICE*

COMPONENTS OF EXTERNAL DEFIBRILLATOR

FIG. 5 — ESTABLISHING LOCAL COMLINK (MOBILE DEVICE INITIATIVE)

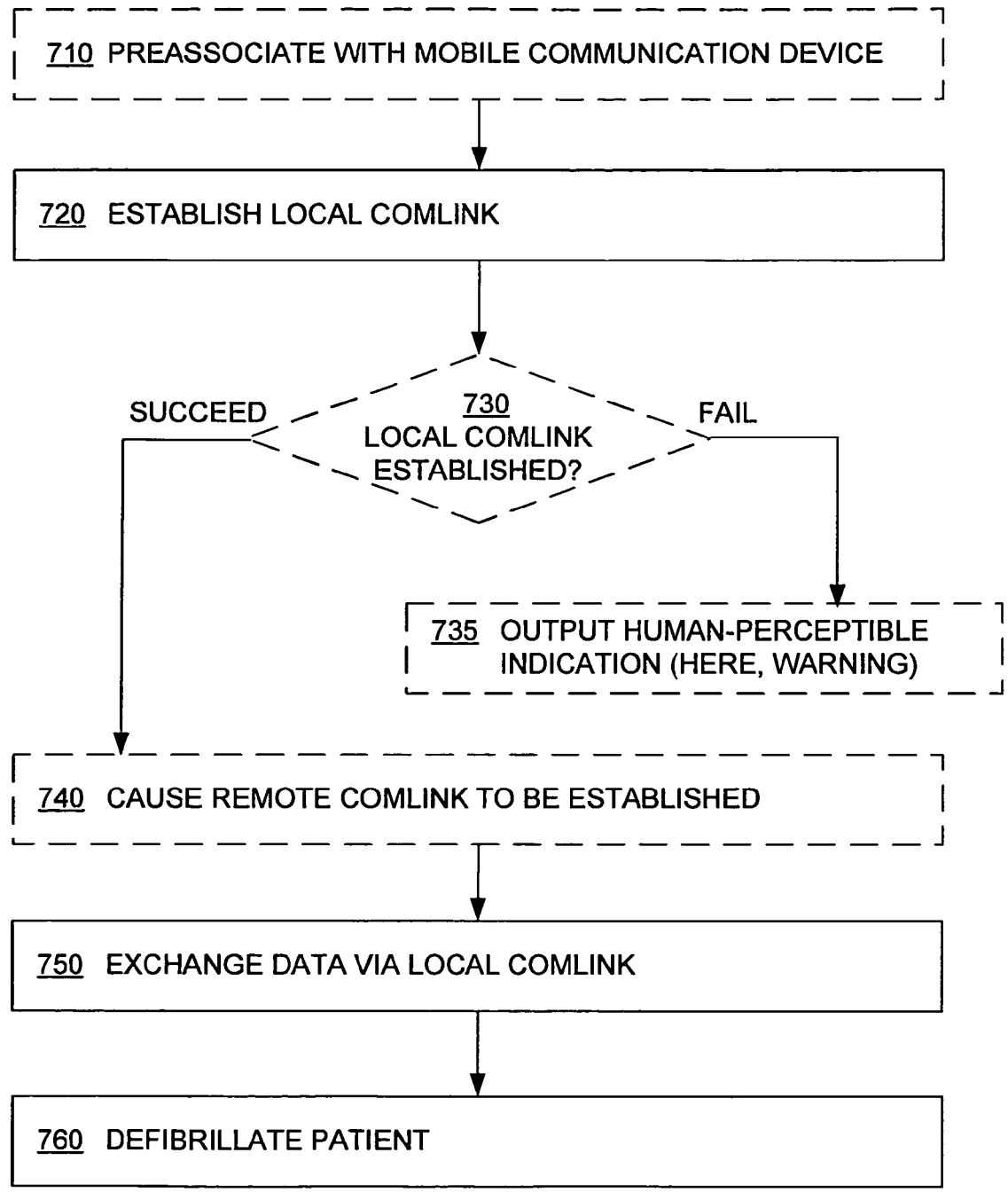

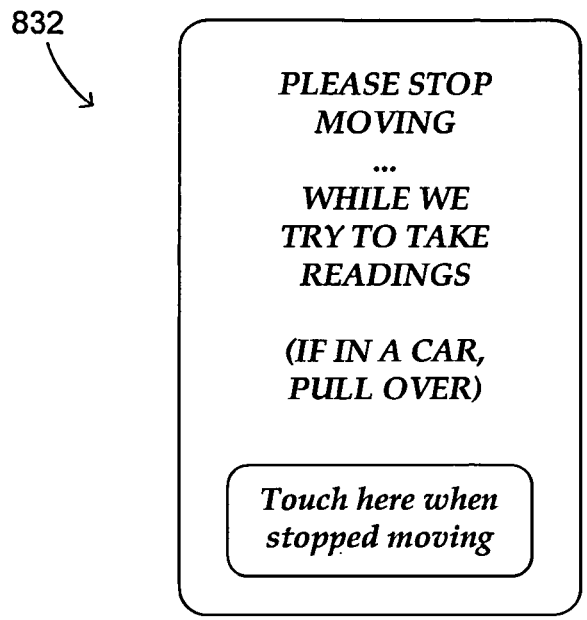
FIG. 8  SCREEN IMAGE
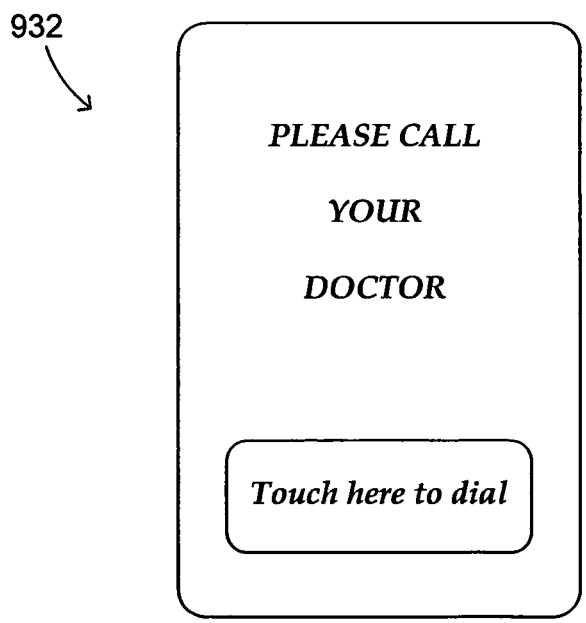
FIG. 9  SCREEN IMAGE

SAMPLE COMPONENTS

WEARABLE DEFIBRILLATOR SYSTEM COMMUNICATING VIA MOBILE COMMUNICATION DEVICE

CROSS REFERENCE TO RELATED PATENT APPLICATIONS

This patent application claims priority from U.S. Provisional Patent Application Ser. No. 61/768,897, filed on Feb. 25, 2013, titled: "WEARABLE DEFIBRILLATOR EXPANDED USER INTERFACE AND COMMUNICATIONS VIA SMART PHONE", the disclosure of which is hereby incorporated by reference for all purposes.

This patent application claims priority from U.S. Provisional Patent Application Ser. No. 61/682,143, filed on Aug. 10, 2012, titled: "WEARABLE MONITOR/DEFIBRILLATOR WITH CARDIAC FUNCTION ASSESSMENT FEATURE", the disclosure of which is hereby incorporated by reference for all purposes.

This patent application claims priority from U.S. Provisional Patent Application Ser. No. 61/706,697, filed on Sep. 27, 2012, titled: "WEARABLE DEFIBRILLATOR/MONITOR WITH A USER INTERFACE FOR MEDICAL CARE DETECTION AND INTERVENTION", the disclosure of which is hereby incorporated by reference for all purposes.

This patent application may be found to be related to U.S. patent application Ser. No. 13/959,984, titled "MOBILE COMMUNIICATION DEVICE & APP FOR WEARABLE DEFIBRILLATOR SYSTEM", filed on the same day as the instant application, and assigned to the same assignee.

BACKGROUND

When people suffer from some types of heart arrhythmia, the result may be that blood flow to the various parts of the body is reduced. Some arrhythmias may even result in a Sudden Cardiac Arrest (SCA). SCA leads to death very quickly, e.g. within 10 minutes, unless treated in the interim.

People who have had a heart attack have an increased risk of SCA, and therefore it is recommended that they receive an Implantable Cardioverter Defibrillator ("ICD"). An ICD has internal electrodes, and continuously monitors the person's electrocardiogram ("ECG"). If certain types of heart arrhythmia are detected, then the ICD delivers electrical therapy through the heart.

People with increased risk of an SCA are sometimes given a wearable external defibrillator system. The recipients typically include those who have had a heart attack, or SCA, or are considered at risk, but have not yet had an ICD implanted. A wearable defibrillator system typically includes a harness, vest, or other garment for wearing by the patient. The system includes a defibrillator and external electrodes, which are attached on the inside of the harness, vest, or other garment. When the patient wears the system, the external electrodes contact the person's skin, and therefore can help monitor the patient's ECG. If a shockable heart arrhythmia is detected, then the defibrillator delivers the appropriate electrical discharge through the heart.

Wearable defibrillator systems stand to improve if they communicate better with their environment.

BRIEF SUMMARY

The present description gives instances of systems, devices, software and methods, the use of which may improve on the prior art.

In some embodiments, a wearable defibrillation system can establish a local comlink with a mobile communication device, such as a smartphone, tablet-type computer and the like. The mobile communication device can in turn establish a remote comlink with other devices in a network such as the internet. Accordingly, communication tasks relating to the wearable defibrillation system can be performed via the local and the remote comlinks, with or without the participation of the wearer. An advantage is that the wearer can use the familiar interface of a mobile communication device for interacting with his wearable defibrillator system. Moreover, the patient can do so while keeping on his regular clothes, which could conceal completely the wearable defibrillator system. As such, the patient can interact with, and enable the interactions of, the wearable defibrillator system while appearing to be using his ordinary, commercially available mobile communication device, and thus preserving their dignity and privacy.

These and other features and advantages of this description will become more readily apparent from the following Detailed Description, which proceeds with reference to the drawings, in which:

BRIEF DESCRIPTION OF THE DRAWING

FIG. 7 is a flowchart for illustrating methods for wearable defibrillation systems according to embodiments.

FIG. 8 is a diagram showing a sample image that can be displayed by a mobile communication device, while a wearable defibrillator system is performing an operation of the flowchart of FIG. 7, according to an embodiment.

FIG. 9 is a diagram showing another sample image that can be displayed by a mobile communication device, while a wearable defibrillator system is performing an operation of the flowchart of FIG. 7, according to another embodiment.

DETAILED DESCRIPTION

As has been mentioned, the present description is about systems, devices, software and methods for wearable defibrillation systems to perform their communication tasks. Embodiments are now described in more detail.

Figure 1:
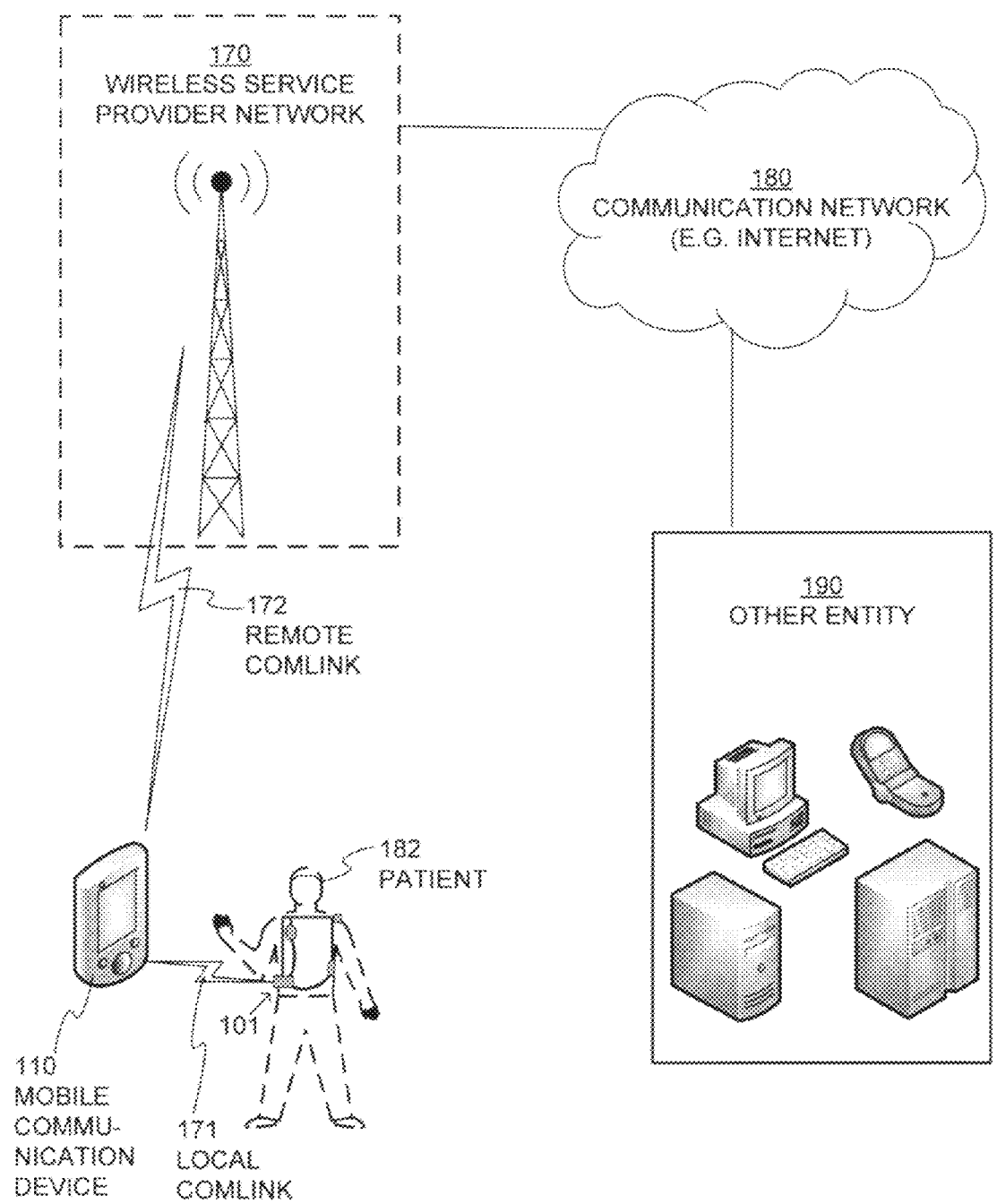
FIG. 1 is a diagram showing a communication arrangement that includes embodiments of the invention.

FIG. 1 depicts a communication arrangement according to embodiments. A patient 182 wears a wearable external defibrillator system 101, and ordinarily carries a mobile communication device 110 on their person. Patient 182 may also be referred to as wearer 182 since he or she wears system 101, person 182, and user 182 since he or she may use device 110.

A mobile communication device such as device 110 can be a wireless telephone, a smartphone, a Personal Digital Assistant (PDA), a personal electronic device, a pager, a laptop computer, a tablet, an e-reader, and so on. Such mobile communication devices are increasingly becoming more than just wireless voice communication devices. In addition to handling voice data, some mobile communication devices are essentially portable computing devices that can support a variety of applications such as email, web browsing, text processing applications, contact applications, scheduling applications, games, and so on.

In many cases, mobile communication device 110 acts as a proxy for also the presence of patient 182. In other words, the location of patient 182 can sometimes be presumed to be the same as the location of mobile communication device 110. Although in most cases device 110 is indeed in close proximity to patient 182, that is not a requirement for carrying out embodiments of the invention.

Patient 182 typically carries mobile communication device 110, and is intended to be its primary user. Patient 182 may carry device 110 in a pocket, in a special holder, or even wear it on their wrist. It should be further remembered that, given the particular dynamics of SCA, where the patient may be an unconscious victim, a rescuer may actually use the patient's mobile communication device 110. And, in some embodiments, a rescuer may instead use their own mobile communication device, instead of the one carried by the victim.

The arrangement of FIG. 1 uses wireless communication links. A wireless communication link is also sometimes referred to as "comlink". For purposes of this document, a "remote comlink" means a wireless communication link established between devices that are at least 500 feet (150 m) away from each other, and typically farther, such as a cellular communication link. And a "local comlink" means a wireless communication link established between devices that are at most 50 feet (15 m) away from each other, and typically closer.

According to the arrangement of FIG. 1, mobile communication device 110 can communicate with a wireless service provider network 170 via a remote comlink 172. Remote comlink 172 can be direct, or can be established between device 110 and network 170 via intermediary points, such as a Wireless Access Point, WiFi, and so on; even in those cases, however, a remote comlink includes at least one leg of a wireless communication link that is at least 500 feet (150 m) long. On or more of the legs between intermediary points may include a network land line. Network 170 can be coupled with a communications network 180, which can be the internet or one of the networks of the internet. An Other Entity 190 can be part of network 180, and in effect be cloud-based. Other Entity 190 can be a person or institution, equipped with any one of a cellular telephone, a desktop computer, a server, a mainframe computer, and so on. Communication devices in Other Entity 190 can also be called remote devices. Accordingly, mobile communication device 110 and/or user 182 are capable of communicating and exchanging data with devices of Other Entity 190, at least according to the arrangement of FIG. 1. Communication can also be verbal, as is known in prior art versions of mobile communication device 110.

In some embodiments, mobile communication device 110 includes an application, also known as an "app", which is not shown in FIG. 1 but will be described later in more detail. In some embodiments, the app becomes downloaded to mobile communication device 110 from Other Entity 190. Downloading is according to the arrangement of FIG. 1, or a different arrangement.

In many embodiments, wearable defibrillator system 101 and mobile communication device 110 are capable of establishing a local comlink 171, and therefore can exchange data between them via the local comlink. Data can be exchanged in either direction, or in both directions. In some embodiments, local comlink 171 uses radio transmission technology that can be broadband and/or shortwave. Local comlink 171 may use Bluetooth technology, Wi-Fi technology, or equivalent. Local comlink 171, coupled with the abilities of mobile communication device 110, enables wearable defibrillator system 101 to communicate better with its environment, as will be seen in more detail later in this document.

In other embodiments, instead of comlink 171, wearable defibrillator system 101 and mobile communication device 110 are capable of establishing a local link that is wired, and therefore can exchange data between them via the wired local link. The wired link can be by any suitable wired connection, for example via a USB or Firewire connection. Such would require the person reaching into their clothes. Communication would be established by the connecting, whereupon the two devices would recognize each other, and so on.

It should be remembered that the person wearing the wearable defibrillator system may be moving, for example during their daily activities. In the evening, they may keep mobile communication device 110 next to their bed, charging. At the same time, they may be recharging the wearable defibrillator system if needed.

Figure 2:
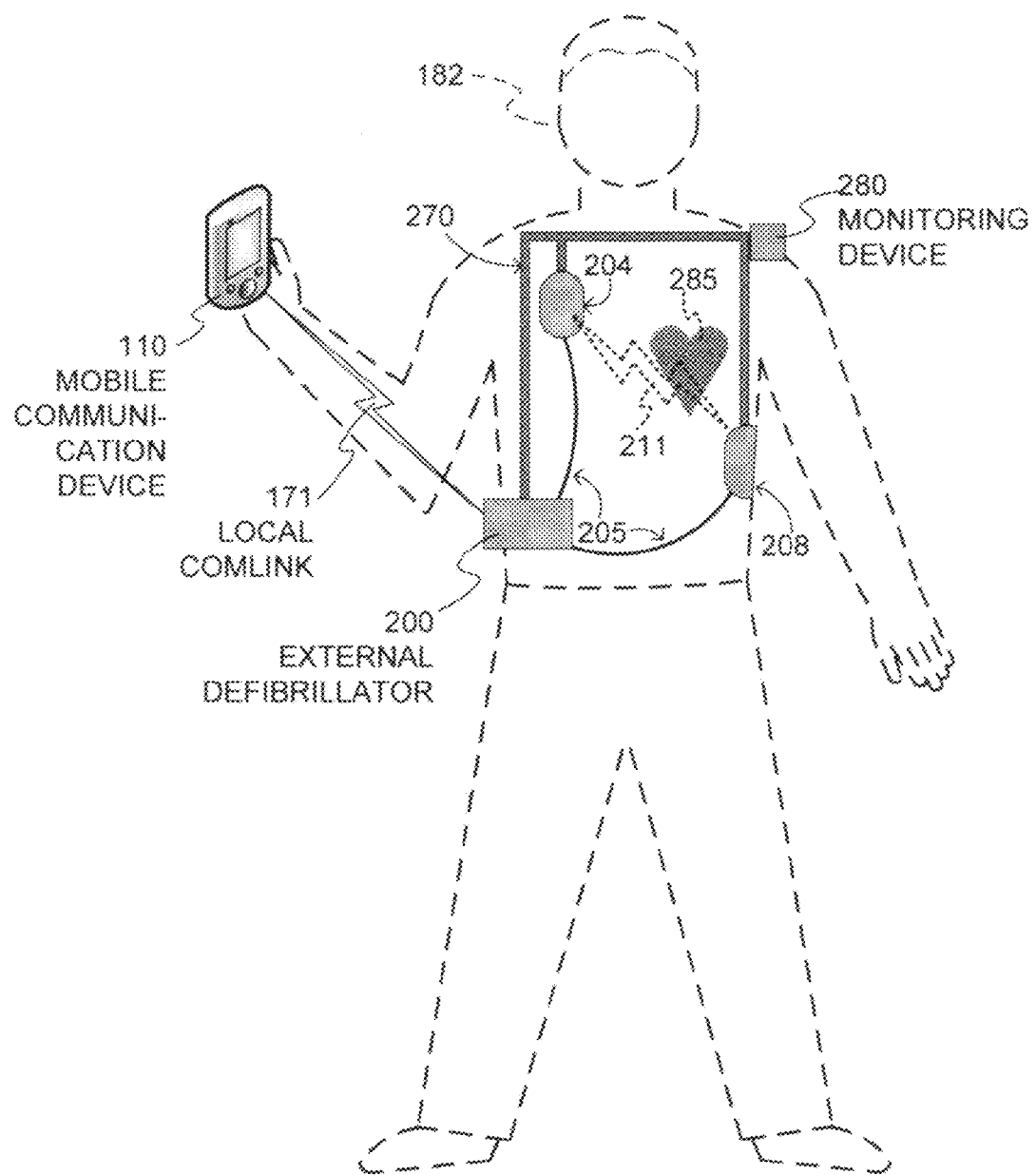
FIG. 2 is a diagram of components of a wearable defibrillator system and a mobile communication device, such as those shown in FIG. 1, which are made and form a local comlink according to embodiments.

FIG. 2 is a diagram of components of a wearable defibrillator system made according to embodiments. For proper context, the components of FIG. 2 are shown as patient 182 would be wearing them. The components of the system of FIG. 2. may be the components of system 101 of FIG. 1.

The components of FIG. 2 include a support structure, which is configured to be worn by patient 182. The support structure can be any structure suitable for wearing, such as a harness, a vest, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around the torso.

Other embodiments could use an adhesive structure or another way for attaching to the person, without encircling any part of the body. There can be other examples.

A generic support structure 270 is shown relative to the body of person 182, and thus also relative to his or her heart 285. Structure 270 could be a harness, vest, garment, as per the above; it could be implemented in a single component, or multiple components, and so on. Structure 270 is wearable by person 182, but the manner of wearing it is not depicted, as structure 270 is depicted only genetically in FIG. 2.

A wearable defibrillator system is configured to defibrillate the person by delivering electrical charge to the person's body. FIG. 2 shows an example of defibrillation electrodes 204, 208, which are coupled to an external defibrillator 200 via electrode leads 205. When defibrillation electrodes 204, 208 make good electrical contact with the body of person 182, defibrillator 200 can administer, via electrodes 204, 208, a brief, strong electric pulse 211 through the body. Pulse 211, also known as a defibrillation shock, goes also through heart 285, in an attempt to restart it, for saving the life of person 182. Defibrillator 200 and defibrillation electrodes 204, 208 are coupled to support structure 270. As such, all components of defibrillator 200 are therefore coupled to support structure 270.

Person 182 is shown holding mobile communication device 110, and device 110 is shown as having established local comlink 171 with one of the components of the wearable defibrillator system. In the example of FIG. 2, local comlink 171 is shown as established specifically with defibrillator 200, on behalf of the entire wearable defibrillator system. This embodiment is advantageous when, as here, defibrillator 200 is collocated with a communication module, but that is not necessary. Indeed, the local comlink can become established with a different component of the system, and particularly the one that includes a wireless communication module on behalf of the entire wearable defibrillator system.

A prior art defibrillator typically decides whether to defibrillate or not based on an electrocardiogram ("ECG") of the patient. However, defibrillator 200 can defibrillate or not also based additionally on other inputs and received communication, as will be seen later. In addition, the use, readiness and maintenance of defibrillator 200 can be improved based on the communication enabled by the invention.

The wearable defibrillator system may also optionally include a monitoring device 280, which can also be called an outside monitoring device. Monitoring device 280 is configured to monitor at least one local parameter. A local parameter is a parameter of patient 182, or a parameter of the wearable defibrillation system, or a parameter of the environment, as will be described later. Optionally, monitoring device 280 is physically coupled to the support structure. In addition, monitoring device 280 is communicatively coupled with other components coupled to the support structure, such as a communication module, as will be deemed necessary by a parson skilled in the art in view of this disclosure.

Figure 3:
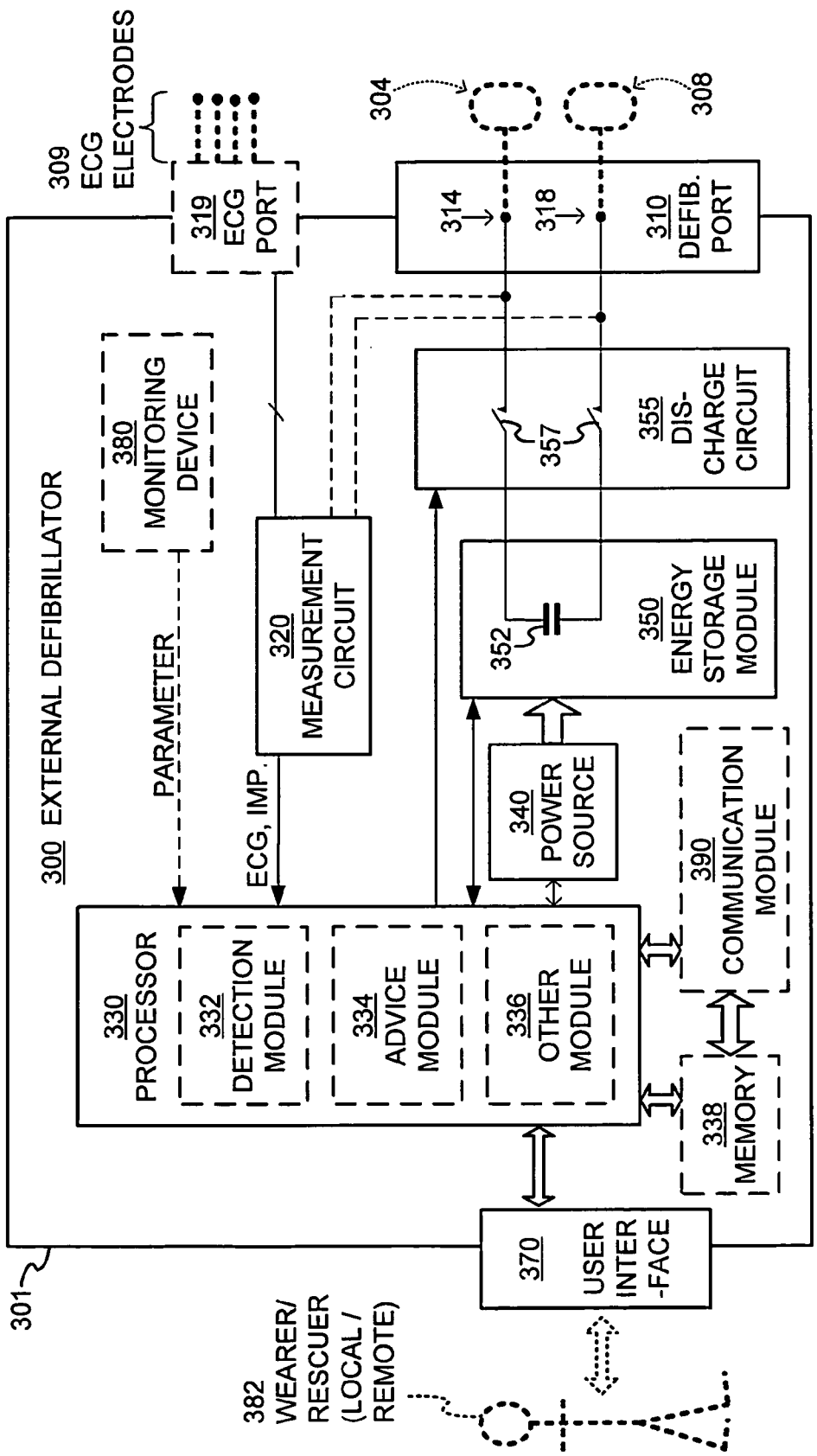
FIG. 3 is a diagram showing components of an external defibrillator, such as the one shown in FIG. 2, and which is made according to embodiments.

FIG. 3 is a diagram showing components of an external defibrillator 300 made according to embodiments. These components can be, for example, in external defibrillator 200 of FIG. 2. The components shown in FIG. 3 can be provided in a housing 301, which is also known as casing 301.

External defibrillator 300 is intended for a patient who would be wearing it, such as person 182 of FIG. 1 and FIG. 2. Defibrillator 300 further includes a user interface 370 for a user 382. User 382 can be wearer 182, if conscious. Or user 382 can be a local rescuer at the scene, such as a bystander who might offer assistance, or a trained person. According to FIG. 1, user 382 might be in remote communication with a remote rescuer, such as a trained person within Other Entity 100, according to embodiments.

Defibrillator 300 may include a monitoring device 380 within housing 301, which can also be called an inside monitoring device. Monitoring device 380 can monitor patient parameters, system parameters and/or environmental parameters. In other words, inside monitoring device 380 can be the same, or complementary to outside monitoring device 280 of FIG. 2, and can be provided in addition to it, or instead of it. Allocating which of the whole system parameters are monitored by which monitoring device can be determined according to design considerations. For example, a motion sensor can be within housing 301, as part of inside monitoring device 380, for system economy based on ease of implementation and communicating its results. For another example, a sensor that monitors the patient's blood pressure may be at the external location of device 280.

Defibrillator 300 typically includes a defibrillation post 310, such as a socket in housing 301. Defibrillation port 310 includes nodes 314, 318. Defibrillation electrodes 304, 308, for example similar to electrodes 204, 208 of FIG. 2, can be plugged in defibrillation port 310. Plugging can be from their leads, such as leads 205 of FIG, 2, so as to make electrical contact with nodes 314, 318, respectively. It is also possible that the defibrillation electrodes can be connected continuously to defibrillation port 310, instead. Either way, defibrillation port 310 can be used for guiding, via electrodes, to the wearer the electrical charge that has been stored in energy storage module 350.

Defibrillator 300 may optionally also have an ECG port 319 in housing 301, for plugging in ECG electrodes 309, which are also known as ECG leads. It is also possible that ECG electrodes can be connected continuously to ECG port 319, instead. ECG electrodes 309 can help sense an ECG signal, e.g. a 12-lead signal, or a signal from a different number of leads, as long as they make good electrical contact with the body of the patient. ECG electrodes 309 can be attached to the inside of support structure 270 for making contact with the patient, similarly as the defibrillation electrodes.

Defibrillator 300 also includes a measurement circuit 320. Measurement circuit 320 receives physiological signals from ECG port 319, if provided. Even if defibrillator 300 lacks ECG port 319, measurement circuit 320 can obtain physiological signals through nodes 314, 318 instead, when defibrillation electrodes 304, 308 are attached to the patient. In these cases, a person's ECG signal can be sensed as a voltage difference between electrodes 304, 308. Plus, impedance between electrodes 304, 308 can be sensed. Sensing the impedance can be useful for detecting, among other things, whether these electrodes 304, 308 are not making good electrical contact with the patient's body. These physiological signals can be sensed, and information about them can be rendered by circuit 320 as data, or other signals, etc.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332.

Processor 330, running detection module 332, is a sample embodiment of a logic device configured to determine whether the above-described monitored parameter has reached a specific threshold. For example, the monitoring parameter can be input from monitoring device 380, if provided. For another example, detection module 332 can include a ventricular fibrillation ("VF") detector. The person's sensed ECG from measurement circuit 320 can be used by the VF detector to determine whether the person is experiencing VF. Detecting VF is useful, because VF is a precursor to SCA.

Another such module in processor 330 can be an advice module 334, which arrives at advice of what to do. The advice can be based on outputs of detection module 332. There can be many types of advice according to embodiments. As one example, a Shock Advisory Algorithm can render the advice to shock, as opposed to not shock the person. Such can be, for example, when the person's condition has reached or exceeded an advised defibrillation threshold. Shocking can be for defibrillation, pacing, and so on.

If the advice is to shock, some external defibrillator embodiments proceed with shocking, or may advise a remote attendant to do it, and so on. As another example, the advice can be to administer CPR, and defibrillator 300 may further issue prompts for it, and so on.

Processor 330 can include additional modules, such as other module 330, for other functions. In addition, if monitoring device 380 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 382, if they are a local rescuer. Moreover, memory 338 can store data. The data can include patient data, system data and environmental data, for example as learned by monitoring device 380 and monitoring device 280. The data can be stored before it is transmitted out of defibrillator 300, or stored after it is received by it.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350, which can thus be coupled to the support structure of the wearable system. Module 350 is where some electrical energy is stored, when preparing it for sudden discharge to administer a shock. Module 350 can be charged from power source 340 to the right amount of energy, as controlled by processor 330. In typical implementations, module 350 includes a capacitor 352, which can be a single capacitor or a system of capacitors, and so on. As described above, capacitor 352 can store the charge for delivering to the patient.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Sounds, images, vibrations, and anything that can be experienced by user 382 can also be called human perceptible indications. Interface 370 may additionally include various controls, such as pushbuttons, keyboards, touchscreens, a microphone, and so on. In addition, discharge circuit 355 can be controlled by processor 330, or directly by user 382 via user interface 370, and so on.

Defibrillator 300 can optionally include a communication module 390, for establishing one or more wireless comlinks, such as local comlink 171. The communication module may also include an antenna, portions of a processor, and other sub-components as may be deemed necessary by a person skilled in the art. This way, data and commands can be communicated, such as patient data, episode information, therapy attempted, CPR performance, system, data, environmental data, and so on.

Defibrillator 300 can optionally include other components.

Figure 4:
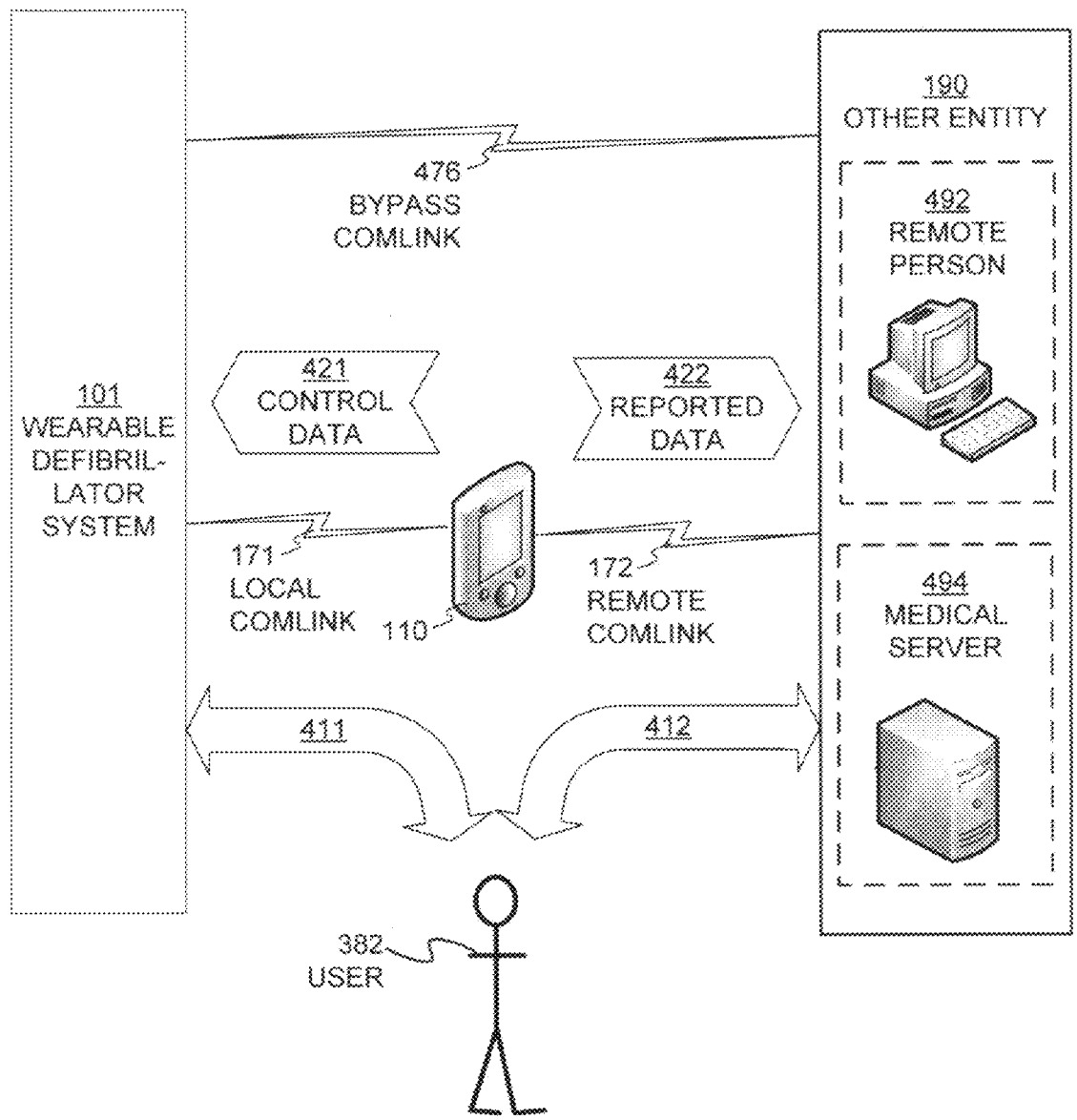
FIG. 4 is a conceptual diagram illustrating ways in which communication links can be established, and the data flows that they enable, according to embodiments.

FIG. 4 is a conceptual diagram illustrating ways in which comlinks can be established, and the data flows that they enable, according to embodiments. One will recognize aspects of the previous figures. User 382 is shown in relation to wearable defibrillator system 101, mobile communication device 110, and Other Entity 190. It should be remembered that user 382 could be either the patient 182 who wears system 101, or a local bystander who is using mobile communication device 110. In addition, in many embodiments. Other Entity 190 includes a remote person 432, and a medical server 494. Person 492 within Other Entity 190 could be a doctor, another caregiver, a health care provider, health care services, dispatch, technical services, a family member, a trusted friend, and so on. Medical server 494 could also include be a repository for data of a person such as a non-medical patient.

More particularly, as already mentioned above, wearable defibrillator system 101 can establish, with mobile communication device 110, a local comlink 171. In addition, mobile communication device 110 can establish, with Other Entity 190, a remote comlink 172. It will be appreciated that the comlinks configured this way, alone or in combination, conveniently permit data flows in different directions.

A data flow can be the two-way data flow 411. More particularly, mobile communication device 110 typically includes a user interface, as is described in more detail later in this document. The user interface at least emits human-perceptible indications, such as sounds, visual indications, images on a screen, and so on for user 382. In some embodiments, the data exchanged via local comlink 171 includes guidance data that is transmitted from the communication module according to flow 411. The guidance data can be emitted by the user interface of device 110 as the human-perceptible indications for user 382.

The feature of the guidance data is particularly useful where the patient's cooperation is desired, if available. One embodiment is with implementing a live man switch. More particularly, a processor of system 101 can be configured to determine that administering a defibrillation shock is advised, for example as described above for processor 330 and advice module 334. The emitted human-perceptible indication can be a request to input a report that the patient is instead alive, such as in the operation of the live man switch, in case the processor's determination happens to not be correct this one time. In that case, if the report is indeed inputted—presumably by the patient—it would mean that the patient is alive, and a defibrillation shock is not needed. Therefore, if the report is indeed inputted, the advised shock may not administered. The feature of the guidance data is useful also in other situations, as will be seen later in this document. The guidance data can also include reminders, such as for service, to charge the battery, to procure disposables, to take medication, for a doctor's appointment, and so on.

Another data flow can be a communication 412 between user 382 and remote person 432. Communication 412 can be a voice conversation, email messaging, texting, and so on. The doctor can query the patient, the patient can ask questions of the doctor, and so on. In addition, communication 412 can be automatically issued reminders by medical server 434, and so on. This way the doctor can monitor the health of the patient.

One more data flow can be control data 421, received via local comlink 171 by wearable defibrillator system 101. As will be appreciated, control data 421 can include data intended to control the actions of wearable defibrillator system 101. In addition, control data 421 can include any data downloaded by medical server 494, which can be maintenance and upgrade data, reprogramming a parameter or setting a software, or commands forcing reporting and the like.

Control data 421 can also include data entered by user 382, as per the above example of the live man switch. Less drastically, system 101 may ask: "Are you feeling all right?", based upon physiological inputs. Moreover, user 382 may enter data according to flow 411 by voice, which may be decoded by voice recognition, and so on. This date may also be answers to routine periodic questions that the defibrillator poses, such as "How are you feeling today?", "Did you take your medication today?", "What is your weight this Monday?", and so on. The answers can then be reported to the doctor later by system 101. Some of this information can thus be exchanged verbally this way. In other embodiments, such information can be captured by sensors, such as a scale for the person's weight, and be transmitted electronically.

In some embodiments, the communication is originated by patient 182, who acts as user 382 of FIG. 4. This enables patient 182 to originate the entry of information about ailments that system 101 might not be prepared to look for automatically. For example, sometimes a patient's condition could be deteriorating despite basic vital signs that are stable, or changing too slowly to raise an alarm. For instance, such could be the case when patient 182 is diagnosed also with heart failure. While system 101 may detect end treat an eventual episode of lethal cardiac arrhythmia, there may be additional conditions for which patient 182 should seek medical care that may not be as critical or sudden as arrhythmias.

In some embodiments, wearable defibrillator system 101 is capable of additional disease management and patient care. Regardless of whether the entry of information is originated by patient 182 or system 101, the patient may enter status data. For example patient 182 may enter a menu where he can select the generic option: "I don't feel good", or "my heart is racing", or "I can't catch my breath". System 101 may consider the patient status data, and evaluate a set of parameters against baseline values that have been recorded in the past. These baseline values may be stored in system 101, or remotely accessed. For example, parameters to evaluate include a) the current status of occurrence and frequency of premature ventricular contraction (PVCs), b) changes in breathing pattern, c) changes in heart rate variability, and so on. These parameters can be learned from monitoring, whether continuously, or upon request, or when a certain mode if activated. If any of those vary more than a preset amount from baseline values for this patient, functions can be triggered that may be stratified based on severity. One of the triggered functions can be that system 101 gives feedback to patient 182, for example via local comlink 171 as human perceptible indications. The feedback can be for patient 182 to manage his condition following physician orders. If system 101 has access to the physician's orders, it may further ask questions such as: "Did you take medication X?", and "Are you keeping your physical activity within range Y?". System 101 may remind patient 182 of the physician's orders, and encourage compliance. Other feedback can be that patient 182 should consult with a professional caregiver within so much time, like immediately or the next 24 hours.

In some embodiments, a language translation module is included in one of various places in this arrangement. The language translation module can be within wearable defibrillation system 101, within mobile device 110, and so on. One example is when a translation module is used for the menu where the patient enters data. While the questions, commands, and prompts could be programmed in a first language, they might appear in a second language that may be chosen in a language menu. Another example is when the patient is unconscious, and user 382 is a helpful bystander who has picked up device 110 and is trying to communicate through it. An example is described later in this document.

The additional disease management and patient care could be provided as a separate mode. The mode can be reset by the patient, or by caregivers, or according to rules. In some embodiments, patient 182 may be given the option to disable the alert to the care management center.

Control data 421 can also include any data received by remote person 492. In some embodiments, remote person 492 may force reporting by system 101. In some embodiments, remote person 492 may outright override the autonomous operation of system 101, and intervene. More particularly, in some embodiments, wearable defibrillator system 101 includes a number of components, such as the components above. For overriding, an operation of a certain one of these included components becomes adjusted due to receiving the control data. Examples of overriding are to activate the defibrillator remotely, or to deactivate it remotely, for example if it is administering shocks where it should not. In each case, the person skilled in the art will determine which one or more components can be the certain components whose operation can be adjusted responsive to the receipt of the control data, for achieving the overriding.

One more of the data flows can be reported data 422, which is received via remote comlink 172 by Other Entity 190. Reported data 422 can include any data reported by system 101 via local comlink 171 and forwarded by mobile communication device 110, which can include all data generated by monitoring devices 280, 380, and/or stored in memory 338. Reported data 422 can include any data gleaned from mobile communication device 110 itself, by virtue of what device 110 permits normally to be gleaned, plus what it generates as part of a custom software application ("app"), made according to embodiments. Reported data 422 can further include anything that user 382 reports live in a communication 412 with remote person 492. Of course, where reported data 422 is patient data, measures should be taken for the appropriate protection of privacy, such as encrypting, removing identification ("de-identifying"), and so on.

More particularly, monitoring devices 280, 380, and measuring circuit 320 sense what are called one or more local parameters. Reported data 422 can include the local parameters. Local parameters include patient physiological parameters, patient state parameters, system parameters and environmental parameters, each of which is discussed individually below.

Patient physiological parameters include, for example, those physiological parameters that can be of any help in detecting by the wearable defibrillation system whether the person is in need of electrotherapy, plus optionally their history. Example such parameters include the person's blood oxygen level, blood flow, blood pressure, blood perfusion, pulsatile change in light transmission or reflection properties of perfused tissue, heart sounds, breathing sounds and pulse. Accordingly, appropriate monitoring devices could be a pulse oximeter, a Doppler device for detecting blood flow, a cuff for detecting blood pressure, illumination detectors and maybe sources for detecting color change in tissue, a device that can detect artery wall movement, a device with a microphone, and so on. Pulse detection is taught at least, in Physio-Control's U.S. Pat. No. 8,135,462, which is hereby incorporated by reference in its entirety. In addition, a person skilled in the art may implement other ways of performing pulse defection.

In some embodiments, the local parameter is a trend that can be detected in a monitored physiological parameter of patient 182. A trend can be detected by comparing values of parameters at different times. Parameters whose detected trends can particularly help a cardiac rehabilitation program include: a) cardiac function (ejection fraction), b) heart rate variability at rest or during exercise, c) heart rate profile during exercise and measurement of activity vigor, such as from the profile of an accelerometer signal and informed from adaptive rate pacemaker technology, d) heart rate trending, e) perfusion, such as from SpO2, CO2, f) respiratory function, respiratory rate, etc., g) motion, level of activity, and so on. Once a trend is detected, it can be reported as part of the data exchanged over via one of the comlinks, along perhaps with a warning. From the report, a physician monitoring the progress of patient 182 will know about a condition that is not improving or deteriorating. In some instances, the physician can tailor more accurately the prescribed medical therapy (medication) and exercise regimen (prescribed physical activity program). That is because the course of treatment post-discharge for the post-Myocardial infarct patient hinges greatly on the improvement and recovery progress and return of cardiac function.

Patient state parameters include the person's motion, posture, whether they have said anything recently, and so on, plus optionally the history of these parameters. The monitoring device may include a motion detector, which can be made in many ways as is known in the art. Or, the monitoring device could include a GPS, which informs of the location, and the rate of change of location over time. Many motion detectors output a motion signal that is indicative of the motion of the detector, and thus of the person's body. Patient state parameters can be very helpful in narrowing down the determination of whether SCA is indeed taking place. For example, it is known how to infer the activities and likely severity of the patient condition by interpreting motion signals. For instance, if the person stops moving at a time when they are expected to be moving or continue moving, or exhibits other behavior that indicates that SCA may be taking place, that can be cause for increased scrutiny, and initiative to contact the patient and/or a remote doctor.

In some embodiments, both the person's physiological parameters and state parameters can be monitored in combination. The value of the physiological parameter becomes better informed from the motion profile, as is the appropriate threshold for determining whether an actionable episode is taking place so as to escalate. The threshold can be adjusted accordingly. For example, if the person is running, then a somewhat higher pulse rate may be tolerated until a time after they stop, without needing to escalate, and so on.

System parameters of wearable defibrillation system 101 can include system identification, battery status, system date and time, reports of self-testing, records of data entered, records of episodes and intervention, and so on.

Environmental parameters can include ambient temperature and pressure. A humidity sensor may provide information as to whether it is raining. Presumed patient location could also be considered an environmental parameter. The patient location could be presumed if monitoring device 280 or 380 includes a Global Positioning System (GPS) sensor. Alternately, presumed location data can be gleaned from mobile communication device 110 and reported.

The exchanged data via local comlink 171 can thus be patient status data, whether it is self-reported, or sensed by system 101. From considering the severity of the patient status data, another triggered function can be that system 101 decides that Other Entity 190 should be notified, and when that should be done. As such, system 101 may further select one of at least two possible notifying times, based on the patient status data. At the selected notifying time, system 101 may then establish the remote comlink 172 or bypass link 476. Such establishing can be automatic, or while involving the patient, for example as is described elsewhere in this document. Once the attempted comlink is indeed established, Other Entity 190 can be notified, and perhaps also receive the patient status data, possibly with annotations for context, and so on. The notified caregiver within Other Entity 190 would then make an assessment, and determine what needs to be done. If the patient status data suggests the patient condition is urgent, the selected notifying time should be as soon as possible. Other suggested conditions can wait longer, for example be part of routine notifying, such as periodic notifying. The selection of the notifying time can be subject to additional rules. In addition, who exactly is notified within Other Entity 190 can also be based on rules for triaging based on the patient status data. The benefit is that a deteriorating condition may be treated earlier than otherwise.

While the above has been mentioned for use with a mobile communication device 110, the invention is not so limited. In other embodiments, wearable defibrillator system 101 can establish a local comlink with a home security alarm system, a vehicle communication system, an in-flight airplane Wi-Fi internet connection, and so-on. The home security alarm system application could be advantageous if the system is landline connected in an area of marginal cellular coverage. System 101 could trigger an alarm and response via Wi-Fi to the home security alarm system, the vehicle communication system—such as OnStar®—and the airplane Wi-Fi internet connection. Accordingly, much of what has been written about mobile communication device 110 in this document can also apply to a home security alarm system, a vehicle communication system, and an airplane Wi-Fi internet connection.

Figure 5:
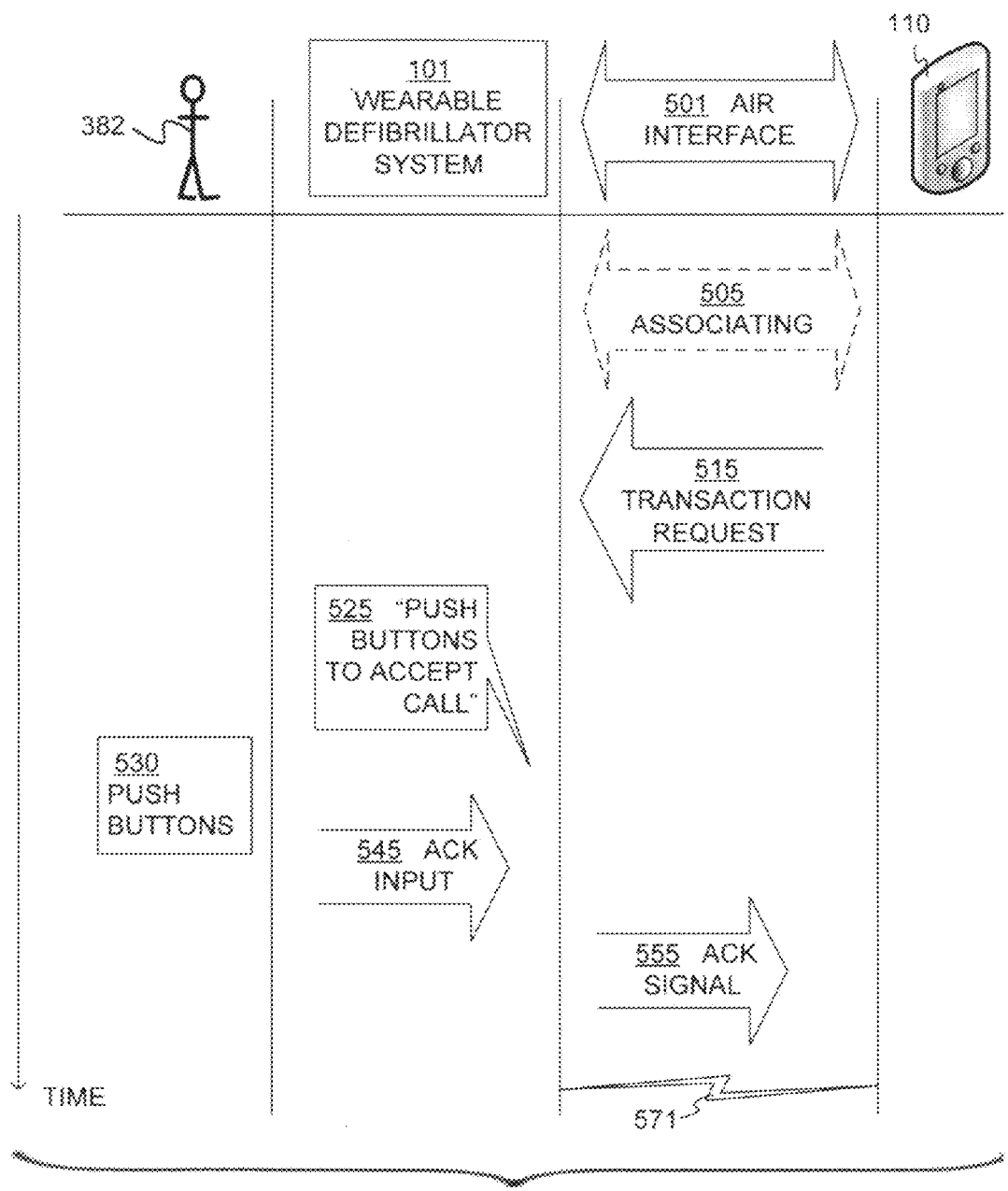
FIG. 5 is a conceptual diagram illustrating sample preliminary operations for establishing a local comlink, according to a first set of embodiments where the initiative is taken by the mobile communication device.

FIG. 5 is a conceptual diagram illustrating sample preliminary operations for establishing a local comlink 571 that is akin to local comlink 171. Such preliminary operations are sometimes also known as "handshake". In this set of embodiments, the initiative for the handshake is taken by mobile communication device 110.

In FIG. 5, the preliminary operations are depicted generally along a vertical time axis. User 382 is depicted next to wearable defibrillator system 101. System 101 is depicted as separated from mobile communication device 110 by an air interface 501. In other words, the exchanges of the handshake between system 101 and device 110 are over the air, i.e. by wireless signals.

In optional and preferred embodiments, wearable defibrillation system 101 is associated with mobile communication device 110 in advance of establishing local comlink 571. Such advance associating 505, also known as pre-associating, will address some of the concerns about security, and quick establishment of the local comlink. Indeed, establishment may have to happen quickly in the event of an emergency. Advance associating is convenient when device 110 is that of the patient, and associating performed by the doctor, when the patient first receives wearable defibrillation system 101. Associating may also happen indirectly, when device 110 downloads an app, which is described later in this document.

In many embodiments, mobile communication device 110 transmits a transaction request 515, so as to initiate the establishment of local comlink 571. Accordingly, local comlink 571 becomes established if wearable defibrillator system 101, and more specifically one of its communication modules, receives transaction request 515 over air interface 501. In some embodiments, local comlink 571 can be established immediately upon such receipt, but care should be taken about security and privacy. As such, in many embodiments, a validity criterion of the received transaction request 515 is first checked; and then local comlink 571 becomes established if transaction request 515 additionally meets that validity criterion.

There are a number of possibilities for implementing the validity criterion. One example is where there has been associating 505. The associating will have informed the devices about each other. Another example of a validity criterion is to inform, in advance, wearable defibrillator system 101 of the identity of possible devices that might emit transaction request 515. One more example is determining whether transaction request 515 has the right password for system 101. Passwords can be updated during off hours, as part of other downloads and so on. Many of these possibilities are for checking the validity criterion automatically, without burdening user 382.

Yet another example for implementing the validity criterion is with the participation and authorization of user 382. In some embodiments, a user interface of wearable defibrillator system 101 is configured to output a human-perceptible indication, when it receives the transaction request. The human-perceptible indication can be an image, but is preferably a vibration or sound so as to get the user's attention. The sound could invite the user to do something specific, so as to indicate his assent about the local comlink being established. In the example of FIG. 5, the human-perceptible indication is a sound 525; upon hearing it, user 382 pushes buttons on system 101 according to operation 530. The button-pushing, or other such action, is received as an ack input 545 at the user interface of system 101. ("ack" is a short for "acknowledgement".) Accordingly, the local comlink can become established if the user interface additionally receives the ack input, which will have been due to the outputted human-perceptible indication. For concluding the handshake, system 101 can then optionally transmit an ack signal 555 to device 110, in response to transaction request 515, and so on.

There are even more options for implementing the validity criterion according to embodiments. For example, user 382 can be challenged to enter a password, and so on. For another example, device 110 can display a random number, and the human-perceptible indication can also indicate the same number at the same time, which would contribute to the peace of mind of the user about accepting the call.

Figure 6:
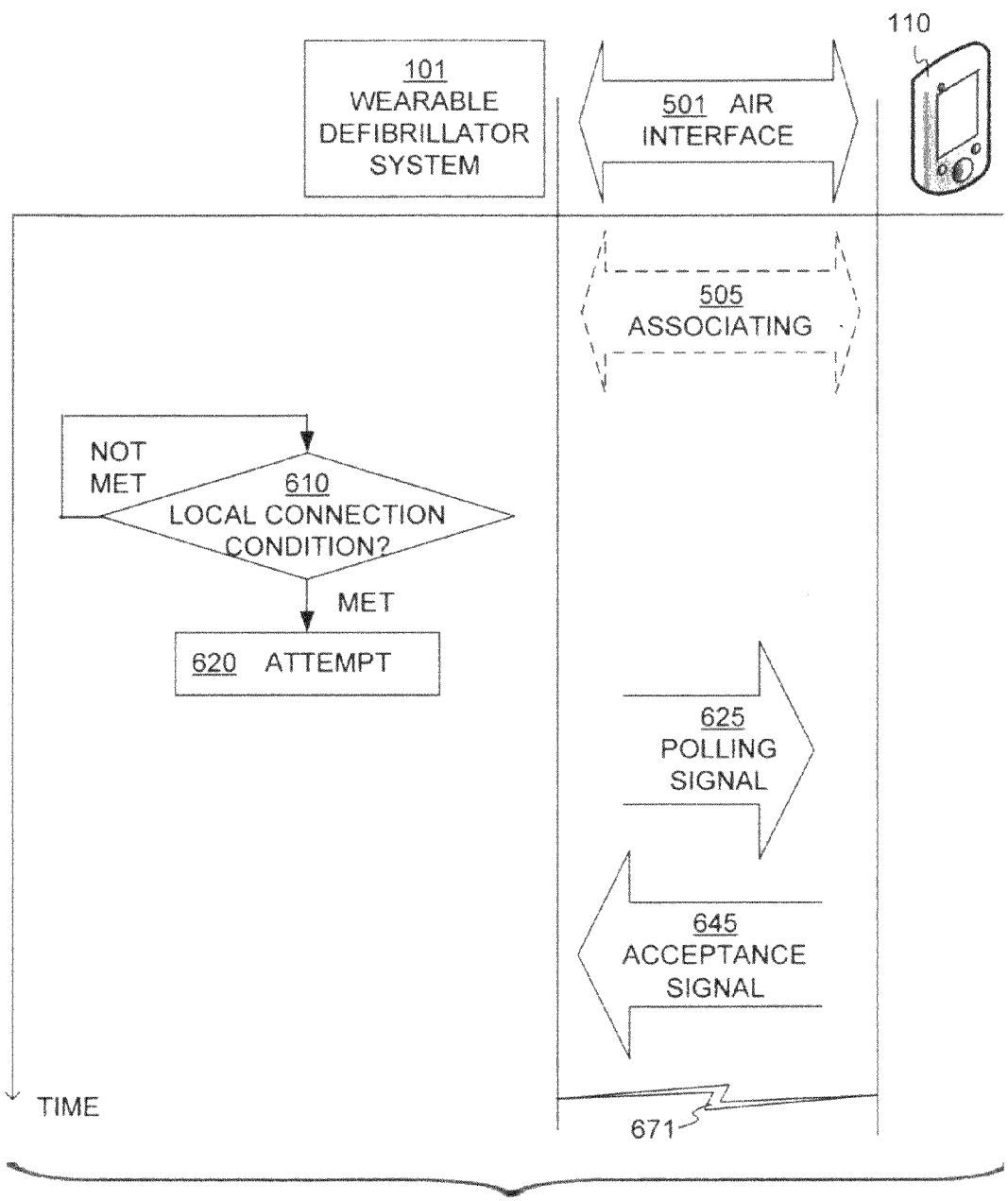
FIG. 6 is a conceptual diagram illustrating sample preliminary operations for establishing a local comlink, according to a second set of embodiments where the initiative is taken by the wearable defibrillator system.

FIG. 6 is a conceptual diagram illustrating sample preliminary operations for establishing a local comlink 621 that is akin to local comlink 171. In this set of embodiments, the initiative for the handshake is taken by wearable defibrillator system 101.

In FIG. 6, the preliminary operations are depicted generally along a vertical time axis. Wearable defibrillation system 101 is depicted as separated from mobile communication device 110 by an air interface 501, as in FIG. 5. In optional and preferred embodiments, system 101 is pre-associated with mobile communication device 110, by performing an operation of associating 505 that was described above with reference to FIG. 5.

In many embodiments, for initiating the establishment of local comlink 671, wearable defibrillator system 101 monitors whether a local connection condition is met. If it is met, then system 101, and more particularly its communication module, is configured to attempt to establish local comlink 671. In FIG. 6 this is shown by a flowchart segment where, according to en operation 610, it is checked whether the local connection condition is met. The operation is in an infinite loop, and does not proceed further, until the condition is met. Then, according to operation 620, the attempt takes place.

The requirement of meeting the local connection condition can be implemented because there may be different reasons for system 101 to initiate the establishment of local comlink 671. One such reason may be that the wearer is having a physiological episode of some sort. For example, as mentioned already above, one of the monitoring devices may sense a local parameter. In that case, the local connection condition can be met if the local parameter exceeds a threshold.

Another reason for system 101 to initiate the establishment of local comlink 671 may be simplicity if the user initiates, at least in terms of security. In such embodiments, a user interface of system 101 can receive a connection input, for example when the user presses a specific button. In that case, the local connection condition can be met if the connection input is received.

In many embodiments, wearable defibrillation system 101 attempts to establish local comlink 671 by transmitting a polling signal 625. In other words, attempt 620 is performed by transmitting a polling signal 625. Polling signal 625 will be received by device 110 across air interface 501. In some of these embodiments, local comlink 671 can be established additionally if an acceptance signal 645 is received, responsive to transmitting polling signal 625.

It will be appreciated that the handshakes of FIG. 5 and FIG. 6 are not mutually exclusive. Rather, both can be operative at the same time, as system 101 and device 110 might demonstrate initiative under different scenarios. In addition, hybrid handshakes can be implemented. For example, according to FIG. 5, device 110 can transmit a transaction request 515. That could meet the local connection condition of operation 610, in which case, according to operation 620, there is an attempt by transmitting polling signal 625.

There are additional possibilities. For one example, if the attempt to establish the local comlink fails, a user interface of system 101 may output a human-perceptible indication, such as an alarming sound. This will notify user 382 that, while their system is trying to communicate the attempt at establishing the local comlink failed.

Moreover, the communication module of system 101 can be further configured to cause remote comlink 172 to also be established automatically. Such embodiments are described later in this document.

At some time, it may be desirable for wearable defibrillation system 101 to terminate communication, for example when all the data that is to be transmitted has indeed been transmitted. Accordingly, in some embodiments, the communication module is further configured to disestablish automatically the local comlink.

Instead of disestablishment, there could also be transition to other modes, such as device 110's "airplane" mode. Device 110 could either automatically go into airplane mode when a condition is met, or require a user input to go into that mode.

Additionally, in some embodiments, the user can terminate the local comlink. This can take place by configuring system 101 to receive a disconnection input from the user. In that case, the local comlink can become disestablished when the disconnection input is received.

Returning to FIG. 4, in some embodiments, a backup functionality is optionally and preferably provided. Wearable defibrillation system 101, and in particular its communication module, is further configured to establish a bypass comlink 476 in addition to comlink 171. Bypass comlink 476 does not include mobile communication device 110. Bypass comlink 475 connects system 101 with one of the other devices in network 180, which could be a device of Other Entity 190. As such, data can be transmitted between system 101 and the other device via bypass comlink 476. The data can be the same as reported data 422, or control data 421, with the same effect as described above with reference to that data.

The backup functionality can be a feature that may be used in an emergency. So, in some embodiments, bypass comlink 470 becomes established if the communication module of system 101 attempts to establish local comlink 171, but the attempt fails. Establishment can be automatic, with or without telling the user, and so on.

The backup functionality can also be a feature that may be used as an alternate. So, in some embodiments, a user interface of system 101 can receive a choice input by user 382, which indicates which of the comlinks—local comlink 171 or bypass comlink 476—is to be used. Accordingly, data can be transmitted via the chosen one of the comlinks instead of the other, responsive to the choice input entered by the user.

The above-mentioned devices and/or systems perform functions and/or methods, as described in this document. The functions and/or methods may be implemented by one or more devices that include logic circuitry. The logic circuitry may include processor 330 that may be programmable for a general purpose, or dedicated, such as microcontroller, a microprocessor, a Digital Signal Processor (DSP), etc. The logic circuitry may also include storage media, such as memory 338. Such a storage medium can be a non-transitory computer-readable medium. These storage media, individually or in combination with others, can have stored thereon programs that the processor may be able to read. The programs can include instructions in the form of code, which the processor may be able to execute upon reading. Executing is performed by physical manipulations of physical quantities.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described. Operations of these methods can also be as described above.

FIG. 7 shows a flowchart 700 for describing methods according to embodiments. The methods of flowchart 700 are for a wearable defibrillation system that is worn by a patient who ordinarily carries a mobile communication device such as device 110. These methods may also be practiced by embodiments described above.

According to an optional operation 710, a wearable defibrillation system is pre-associated with a mobile communication device.

According to a next operation 720, a local comlink is established with the mobile communication device. Establishing can be with the initiative being on either side, as per the above.

According to an optional next operation 730, it is inquired whether the local comlink has indeed become established. If the establishing has failed then, according to optional operation 735, a human-perceptible indication is output, to warn a user.

If the local comlink has indeed become established then, according to an optional next operation 740, a remote comlink is caused to become established.

According to a next operation 750, data is exchanged via the local comlink. Examples were seen with reference to FIG. 4. Of the various data flows, particularly data flow 411 can include guidance data for the user. An example was for when mobile communication device can be used as the live man switch. Two more examples are provided below.

FIG. 8 is a diagram showing a sample image that could be displayed on a screen 832 of a mobile communication device, while the wearable defibrillator system could be performing operation 750 of flowchart 700. The image is due to guidance data received by the mobile communication device according to data flow 411. Depending on the context of use, projecting the image may be accompanied with a vibration or a sound, so as to get the attention of the user. The particular sample image of FIG. 8 can arise if the patient is moving or being moved, such as being in a moving car. The motion would result in, among other things, artifacts in the patient's ECG readings; as such it would be difficult for the wearable defibrillation system to make a decision as to whether a defibrillation shock is advised. Upon seeing the image on screen 832, the wearer would hopefully stop moving, and then wait or even touch screen 832 where indicated.

FIG. 9 is a diagram showing another sample image that could be displayed by a mobile communication device performing an operation of the flowchart of FIG. 7.

FIG. 9, similarly with FIG. 8, is a diagram showing a sample image that can be displayed on a screen 932 of a mobile communication device, while the wearable defibrillator system could be performing operation 750 of flowchart 700. The particular sample image of FIG. 9 can arise if the wearable defibrillator system senses, for example, that the patient is about to have an episode, or an episode is now worsening. Upon seeing the image on screen 932, the wearer would hopefully call remote person 492, and thus be better prepared. In so doing, the patient would be establishing the remote comlink as user 382.

There can be many instances of the images of FIG. 8 and FIG. 9. These images can be better informed by the additionally monitored data. For example, in the instance of FIG. 9, if a pattern of the signal from the motion detector revealed that the wearer is in a car, it might additionally suggest to the wearer that they pull over to the side of the road.

Returning to FIG. 7, according to a next operation 760, the patient may be defibrillated by the wearable defibrillator system. Defibrillation can be as described above.

Figure 10:
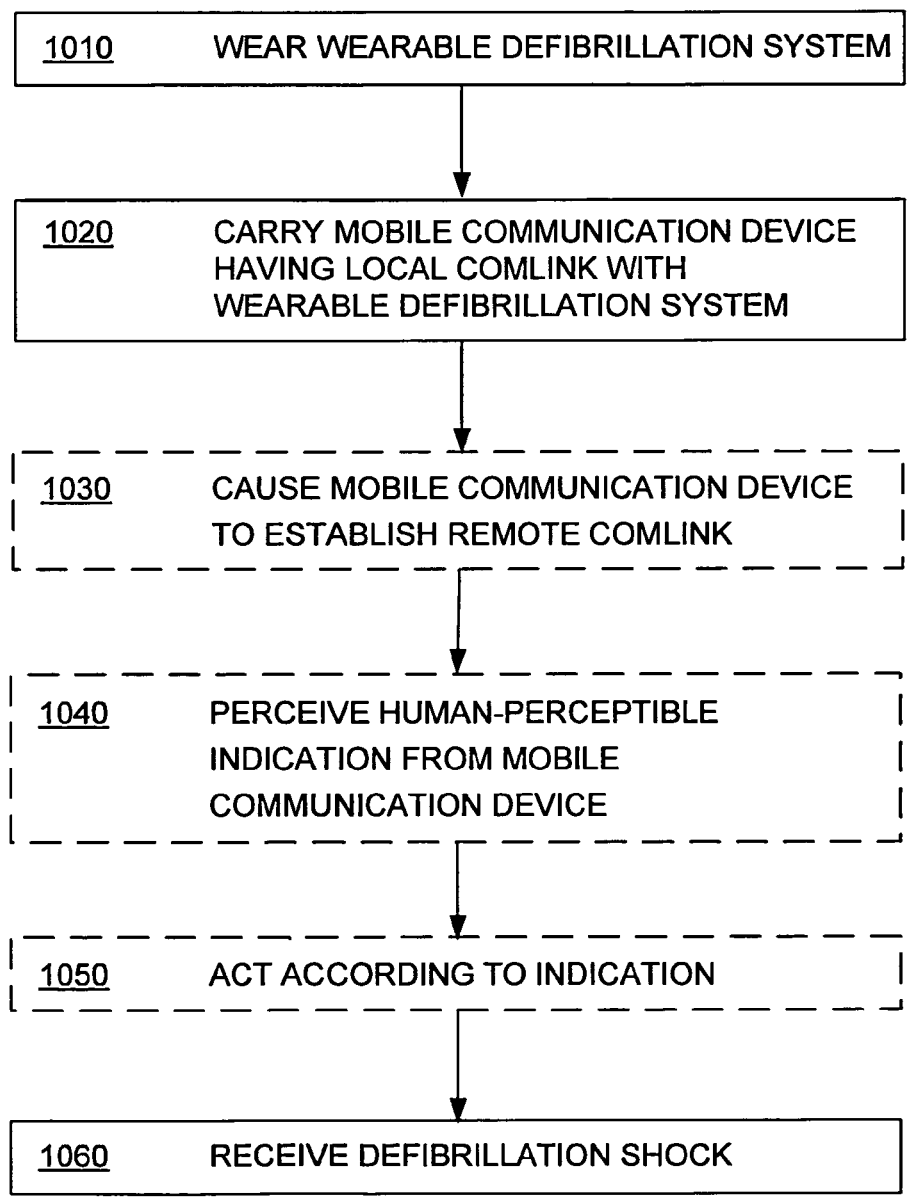
FIG. 10 is a flowchart for illustrating methods for patients according to embodiments.

FIG. 10 shows a flowchart 1000 for describing methods for patients according to embodiments. The methods of flowchart 1000 may also be practiced by patients using embodiments described in this document.

According to an operation 1010, a patient may wear a wearable defibrillation system.

According to a next operation 1020, the patient may carry a mobile communication device, and use it as a user 382. If a language translation module is indeed available, the patient may enter in advance in the mobile communication device a selection of a preferred one of at least two, and possibly many, available languages. The mobile communication device may have established a local comlink with the wearable defibrillation system that the patient is wearing. The patient may also have performed acts to establish the local comlink, and may perform later acts to disestablish it.

According to an optional next operation 1030, the patient may cause the mobile communication device to also establish a remote comlink, in addition to the local comlink. For doing so, the patient may enter a remote access request in the mobile communication device, and so on.

According to an optional next operation 1040, the patient may perceive a human-perceptible indication from the mobile communication device. If the patient has entered in advance his selection of a preferred language, the mobile communication device will use it because of the entered selection, and the human-perceptible indication will be perceived in the preferred language.

According to an optional next operation 1050, the patient may act according to the indication. A number of examples from above are apt also here. First, the human-perceptible indication can be a challenge to the patient, to perform an indicated act so as to prove they are not suffering from SCA. In that case, the patient's acting would be to perform the indicated act. Second, the human perceptible indication can be as in FIG. 8, in which case acting would include the patient reducing an amount of their bodily motion. Third, the human perceptible indication can be as in FIG. 9, in which case acting would include the patient to cause the mobile communication device to establish the remote comlink. It will be appreciated that many such examples could be implemented from different types of guidance data arriving via the local comlink. In some embodiments, guidance data could ultimately be sourcing from other entity 130, such as an intervening doctor, and arriving either via remote comlink 172, or via bypass comlink 476 and local comlink 171.

According to a next operation 1060, the patient may receive a defibrillation shock from the wearable defibrillation system, while wearing it. In addition to the above, a patient may perform what is mentioned elsewhere in this document that can be performed by user 382.

Figure 11:
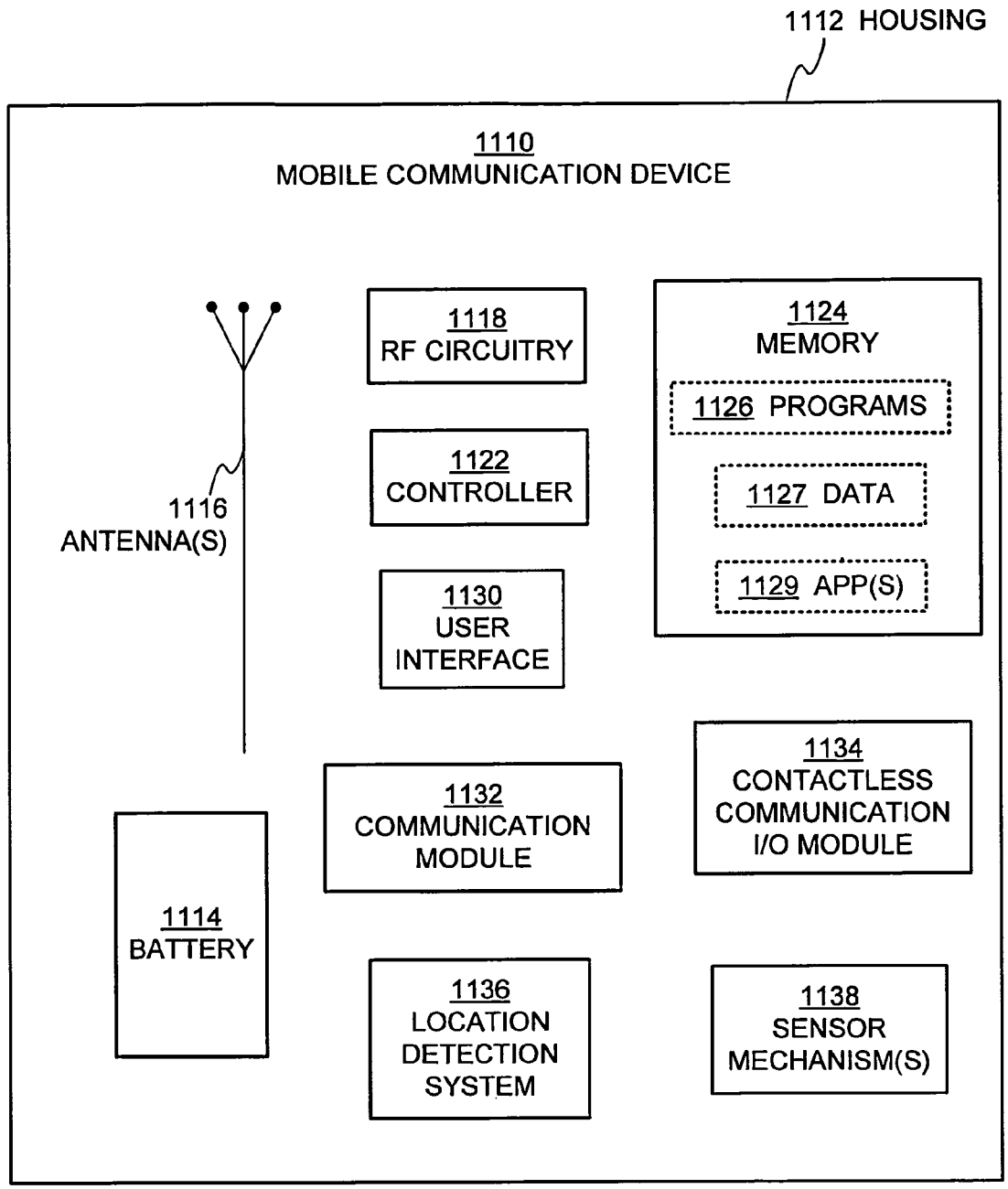
FIG. 11 is a diagram showing sample components of a mobile communication device that could be the device of FIG. 1, and which is made according to embodiments.

FIG. 11 is a diagram showing possible sample components of a mobile communication device 1110. Device 1110 could be the same as device 110 that is depicted in FIG. 1. Mobile communication device 1110 is typically provided with a housing 1112, and its components are typically within housing 1112. Device 1110 is typically powered by a battery 1114 that is rechargeable, for portability of mobile communication device 1110.

Mobile communication device 1110 includes one or more antennas 1116 for wireless communication. Device 1110 also includes RF (radio frequency) circuitry 1118. RF circuitry 1118 cooperates with antenna(s) 1116 to receive and send RF signals. RF circuitry 1118 converts wired electrical signals to/from RF signals. RF circuitry 1118 may include well-known circuitry for performing these functions, including but not limited to an RF transceiver, one or more amplifiers, a tuner, one or more oscillators, a digital signal processor, a CODEC chipset, a subscriber Identity module (SIM) card, a memory, and so forth. The one or more antennas 1116, plus RF circuitry 1118, can establish comlinks as per the above, when cooperating with one of the communication modules of mobile communication device 1110 that are described below.

Mobile communication device 1110 additionally includes a controller 1122, for controlling its operation. Controller 1122 can be one or more processors, implemented as a Central Processing Unit (CPU), a digital signal processor, a microprocessor, a microcontroller, an application-specific Integrated circuit (ASIC), a programmable logic device (PLD) or other implementation. Controller 1122 can be optionally combined in a single chip with a memory controller and a peripherals interface.

Device 1110 also includes a memory 1124, which can include both persistent/non-volatile and non-persistent/volatile memory components. Memory 1124 can be implemented in any technology for memory for such devices, for example RAM, ROM, EEPROM, flash memory, and so on. Additional memory components may be plugged in from a device external to housing 1112, such as a thumb drive, in some embodiments. As such, memory 1124 can include a non-transitory computer-readable storage medium. Memory 1124 can store programs 1126 and data 1127. Programs 1126 can include instructions that can be executed by controller 1122. Programs 1126 may include an operating system, such as, for example, Android, IOS, Windows Phone, Symbian, or Black-Berry OS.

In addition, one or more app(s) 1129 can be stored in memory 1124, as mentioned above. App(s) 1129 can also include instructions that can be executed by controller 1122. Common app(s) 1129 can be provided for a contacts module, an email client module, a calendar module, a camera module, a maps module, and so on.

It will be appreciated that many of the methods of the invention can be performed by mobile communication device 1110 due to one or more special app(s) 1129, in addition to common apps. Even if mobile communication device 1110 is initially provided in a more generic form without special app(s) 1129, the latter may be downloaded later, for example using the communication arrangement of FIG. 1.

Mobile communication device 1110 further includes a user interface 1130, for use by a user, such as user 382. User interface 1130 includes individual devices for receiving inputs by the user, generating outputs for the user, or both. The outputs for the user can be human-perceptible indications, such as sounds, vibrations, lights, images, and so on. Examples of such individual devices include a screen that could be a touch screen, a physical keypad, an optical finger interface, one or more speakers, one or more microphones, one or more accelerometers, and so on. Such devices can be included within housing 1112, or can be added by a separate plugin, such as a keypad, a keyboard, a display, and a speaker.

Mobile communication device 1110 moreover includes a communication module 1132. Module 1132 can conduct communication using any one of a variety of standards, protocols and technologies. Examples of the latter are Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS), and/or Short Message Service (SMS), or any other suitable communication protocol, including communication protocols not yet developed as of the filing date of this document.

Additionally, mobile communication device 1110 can include a contactless communication I/O module 1134. Module 1134 can be used for short range detection and communication, such as Near-Field Communications (NFC), Radio frequency Identification (RIFD), and so on.

Mobile communication device 1110 can also include a location detection system 1136, which can be implemented with GPS. Device 1110 can further include one or more sensor mechanisms 1138. Mechanisms 1138 can include one or more accelerometers, a proximity sensor, a magnetometer, optical sensors, an image sensor, and so on. Data captured by location detection system 1136 and sensor mechanisms 1138 can be stored as data 1127.

Programs 1126, and also app(s) 1129, can advantageously coordinate their use with components of device 1110. For example, and depending on the application, antenna(s) 1116 may be used to detect electromagnetic fields (EMF), and a microphone of user interface 1130 may be used to detect sound. Many of the components of a mobile communication device are well known in the field, and therefore and are not described further.

It will be appreciated that modes of mobile communication device 1110 can be used advantageously according to embodiments. For example, device 1110 could be placed in a video mode for transmitting video m addition to transmitting voice as a telephone. Moreover, device 1110 could be placed in an answer mode, so someone from Other Entity 190 could talk with and listen to a bystander, without requiring the patient to answer the call.

Figure 12:
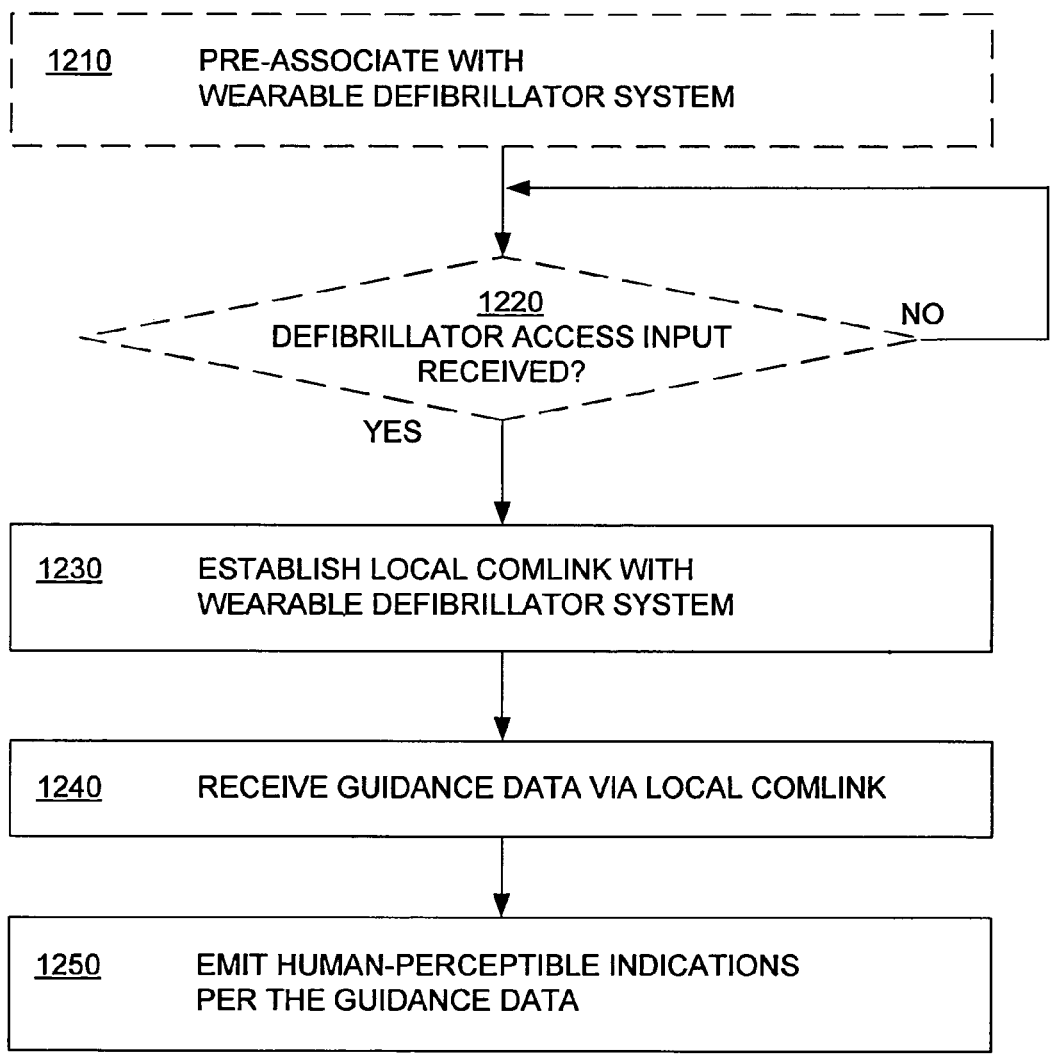
FIG. 12 is a flowchart for illustrating methods for mobile communication devices according to embodiments.

FIG. 12 shows a flowchart 1200 for describing methods according to embodiments. The methods of flowchart 1200 may be practiced by a mobile communication device that can be carried by a user who wears a wearable defibrillation system, such as described above.

According to an optional operation 1210, the mobile communication device can be associated with the wearable defibrillation system.

According to an optional next operation 1220, it can be inquired as to whether a defibrillator access input has been received by the user. Such inputs are received by the user interface of the mobile communication device. The operation is optional, in that it is included in some embodiments but not others. It may not be included in embodiments where it is desired to have some operations be performed automatically.

While a defibrillator access input has not been received, flowchart 1200 does not progress beyond operation 1220, in some embodiments.

According to a next operation 1230, a local comlink is established with the defibrillation system. Operation 1230 can be performed as described above, including also FIGS. 5 and 6. In addition, those processes can be further enhanced by additionally requiring that the mobile communication device first wait for a confirmation input by the user before establishing the local comlink.

According to a next operation 1240, guidance data is received via the local comlink. According to a next operation 1250, human-perceptible indications are emitted per the guidance data. The indications are emitted responsive to receiving the guidance data, and are intended as guidance to the user. These indications are emitted from a user interface of the mobile communication device, for example as shown in FIGS. 8 and 9 above. It will be recognized that while some types of guidance data are intended for the user to do something, other types of guidance data are intended simply for informing the user.

At some time, it may be desirable for the data communication to be terminated naturally. In some instances, wearable defibrillation system 101 may determine that this time has come. In some embodiments, therefore, the local comlink then becomes disestablished by the wearable defibrillation system. In addition, the user may be notified.

In other embodiments, system 101 may ask the user to terminate the communication, or acknowledge that it is being terminated. For example, the emitted human-perceptible indications may indicate that the local comlink may now be disestablished. The indications may further invite the user to enter a termination input. When the termination input is indeed entered, the local comlink can become disestablished.

Figure 13:
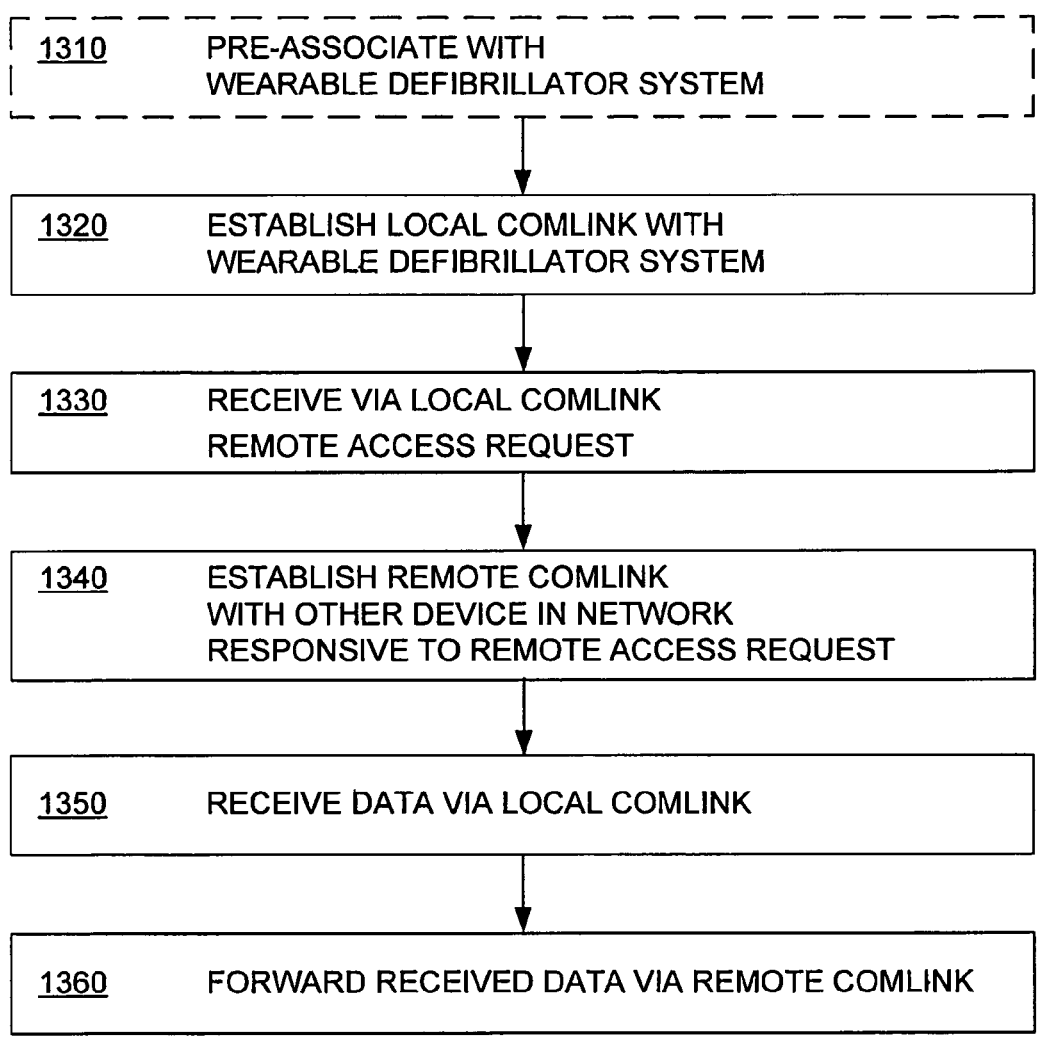
FIG. 13 is a flowchart for illustrating methods for mobile communication devices according to embodiments.

FIG. 13 shows a flowchart 1300 for describing methods according to embodiments. The methods of flowchart 1300 may be practiced by a mobile communication device that can be carried by a user who wears a wearable defibrillation system, such as described above.

Figure 14:
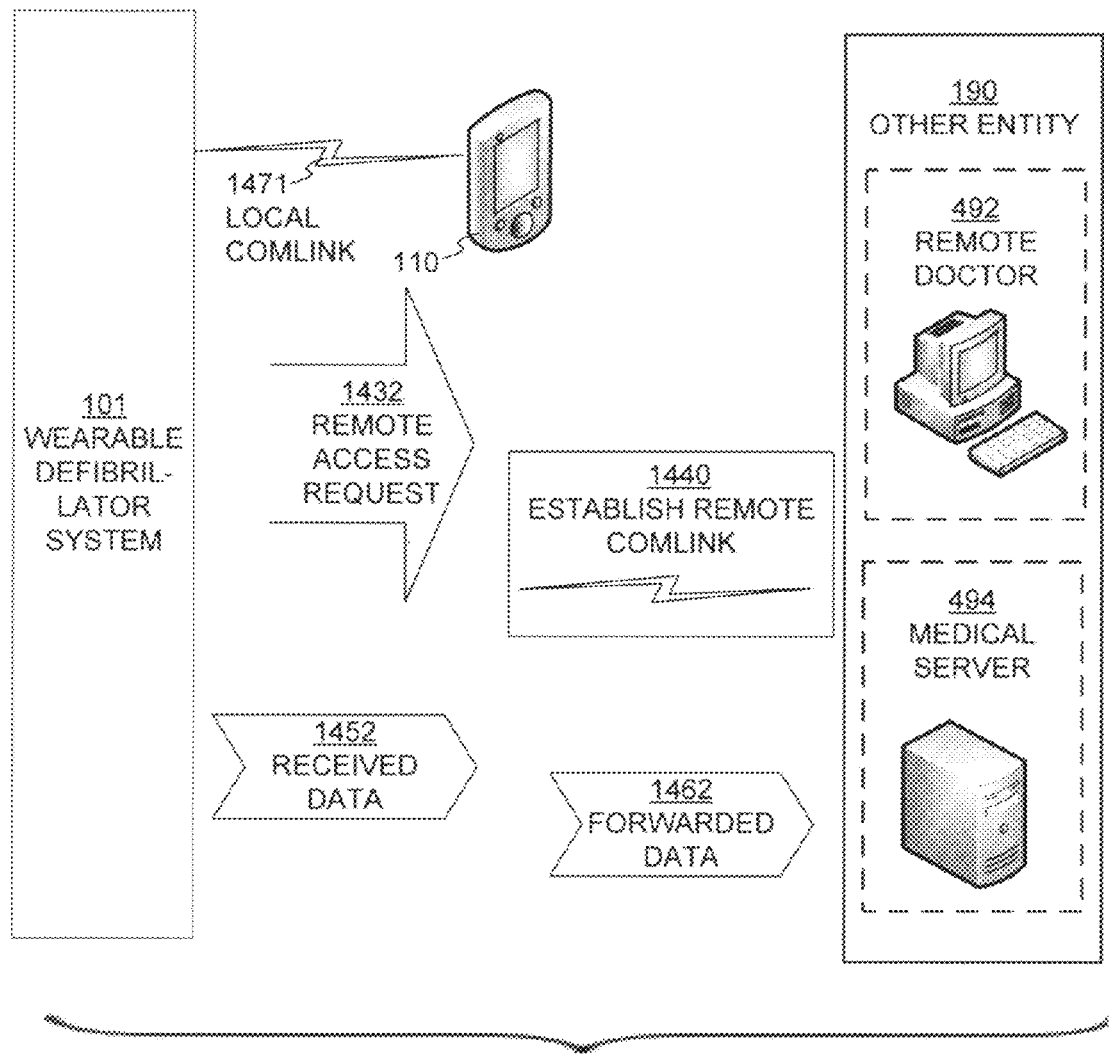
FIG. 14 is a conceptual diagram illustrating ways in which communication links can be established, and the data flows that they enable, according to embodiments of the methods of FIG. 13.

FIG. 14 is a conceptual diagram illustrating ways in which comlinks can be established, and the data flows that they enable, according to embodiments of FIG. 13. As such, many of the operations of FIG. 13 will be described together with analogous items in FIG. 14.

According to an optional operation 1310, the mobile communication device becomes associated with the wearable defibrillation system. This operation, which is repeated in other methods, is performed for establishing the local comlink later more easily, as described above.

According to a next operation 1320, a local comlink is established with the defibrillation system. A sample local comlink 1471 is shown in FIG. 14.

According to a next operation 1330, a remote access request is received via the established local comlink. A remote access request 1432 is shown in FIG. 14. The remote access request is a request by a wearable defibrillation system that the remote comlink be established with a device in the network, so that the wearable defibrillation system can ultimately forward data to it, or request data from it. Optionally, a human-perceptible indication is output by the user interface, in response to receiving the remote access request.

According to a next operation 1340, a remote comlink is established, responsive to the remote access request. The remote comlink is with another device in a network. In some embodiments, establishment is without intervention by the user, in other words it is automatic. Even where establishment is automatic there is optional notification to the user, by suitably adapting the optional human-perceptible indication described above with reference to operation 1330. A box for operation 1440, akin to operation 1340, can be seen in FIG. 14.

In some instances, the remote comlink is with a preset other device in another entity, such as Other Entity 190, which is familiar with system 101. In other instances, the remote comlink is with an emergency telephone number. Such a telephone number is "911" in the USA, and there are different numbers in different countries.

According to a next operation 1350, data is received via the local comlink. Such can be seen as received data 1452 in FIG. 14, and could be of the nature of reported data 422 shown in FIG. 4. There can also be data traveling in the opposite direction, in response.

According to a next operation 1360, the received data is forwarded via the remote comlink. Such can be seen as forwarded data 1462 in FIG. 14.

In some embodiments of the forwarding operation, device 110 has a dual communication mode, for both comlinks to be active concurrently. For example, when device 110 has access to a Wi-Fi (or high band width) data connection, all data can be streamed (including continuous ECG), or periodically transmitted, and thus forwarded to Other Entity 190. In the case when Wi-Fi is intermittently available, subsets of the data would be intermittently forwarded. This would be useful in the case of an emergency, when a condition has been detected where help is required. The bandwidth availability and connection availability can be gauged so that a determination can be made as to whether much data can be transmitted, or little. If little data can be transmitted, then a judgment can be made as to which data to transmit. For example, transmission could start with the patient name, condition and location. If more bandwidth is available, perhaps a strip of ECG can be added, and so on.

As with all other methods in this description, the methods of flowchart 1300 can be augmented with additional operations, such as notifying the user of other events by outputting more human-perceptible indications. These other events can be, for example, if the remote comlink falls to become established, or the local or the remote comlink becomes disestablished, when the desired data transmission is complete and it is time to terminate, when one or both of the comlinks may be disconnected, and so on.

Figure 15:
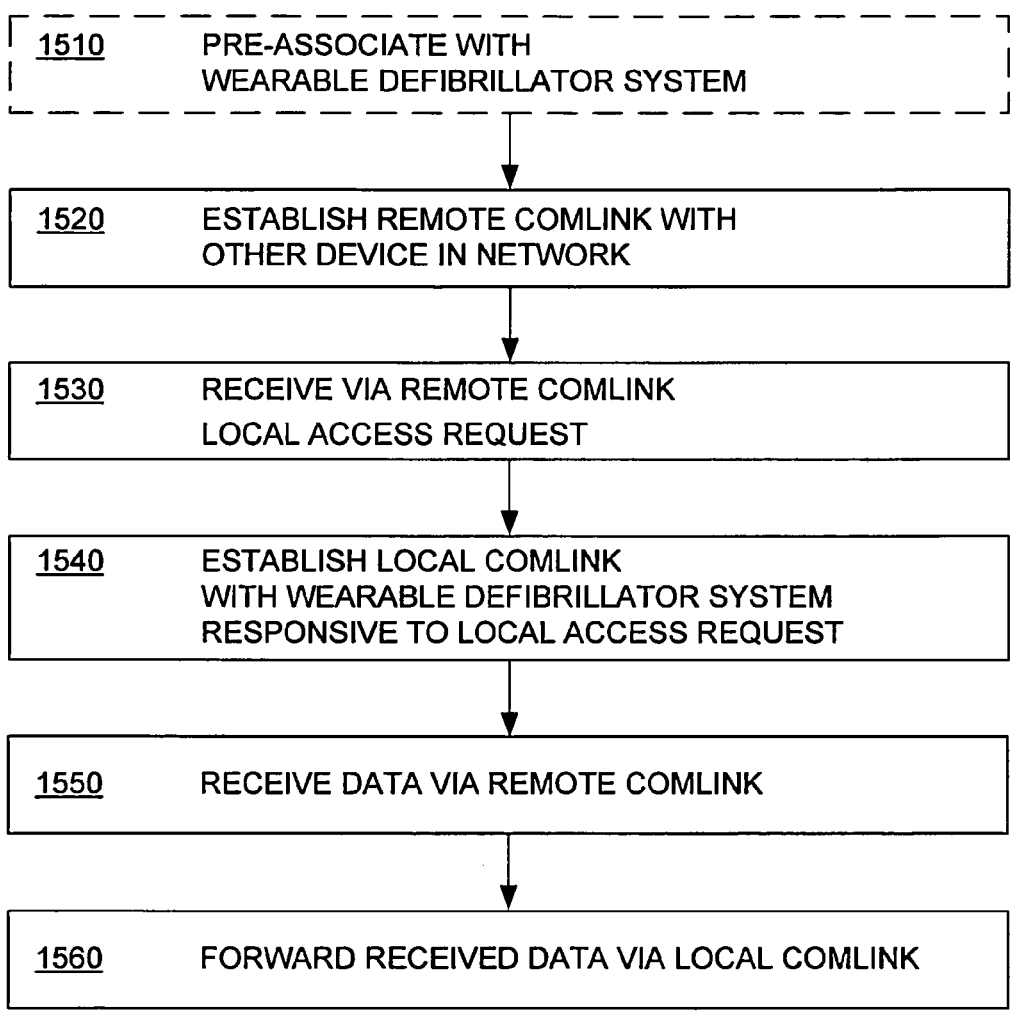
FIG. 15 is a flowchart for illustrating methods for mobile communication devices according to embodiments.

FIG. 15 shows a flowchart 1500 for describing methods according to embodiments. The methods of flowchart 1500 may be practiced by a mobile communication device that can be carried by a user who wears a wearable defibrillation system, such as described above.

Figure 16:
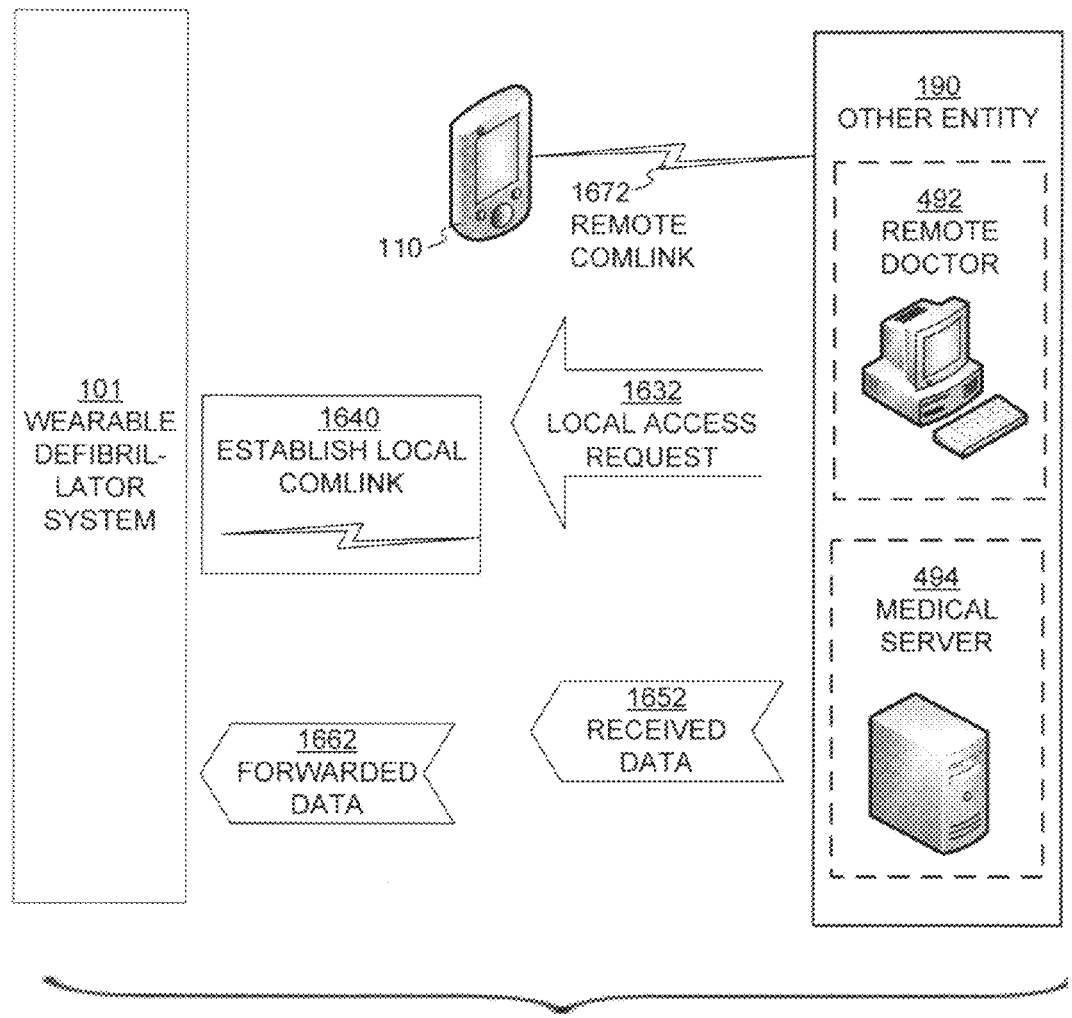
FIG. 16 is a conceptual diagram illustrating ways in which communication links can be established, and the data flows that they enable, according to embodiments of the methods of FIG. 15.

FIG. 16 is a conceptual diagram illustrating ways in which comlinks can be established, and the data flows that they enable, according to embodiments of FIG. 15. As such, many of the operations of FIG. 15 will be described together with analogous items in FIG. 16.

According to an optional operation 1510, the mobile communication device can be associated with the wearable defibrillation system.

According to a next operation 1520, a remote comlink is established with another device in a network. A sample local comlink 1072 is shown in FIG. 16.

According to a next operation 1530, a local access request is received via the established remote comlink. A local access request 1632 is shown in FIG. 16. The local access request is a request by another network device within Other Entity 190 that the local comlink be established with the wearable defibrillation system, so that the other network device may ultimately forward data to it, or request data from it. Optionally, a human-perceptible indication is output by the user interface, in response to receiving the local access request.

According to a next operation 1540, a local comlink is established, responsive to the local access request. The local comlink is the wearable defibrillator system, in some embodiments, establishment is without intervention by the user, in ether words it is automatic. Even where establishment is automatic there is optional notification to the user, by suitably adapting the optional human-perceptible indication described above with reference to operation 1530. A box for operation 1640, akin to operation 1540, can be seen in FIG. 16.

According to a next operation 1550, data is received via the remote comlink. Such can be seen as received data 1652 in FIG. 18, and could be of the nature of control data 421 shown in FIG. 4. There can also be data traveling in the opposite direction, in response.

According to a next operation 1560, the received data is forwarded via the remote comlink. Such can be seen as forwarded data 1662 in FIG. 16.

Moreover, the methods of flowchart 1500 can be augmented as above, and especially as the methods of flowchart 1300.

Figure 17:
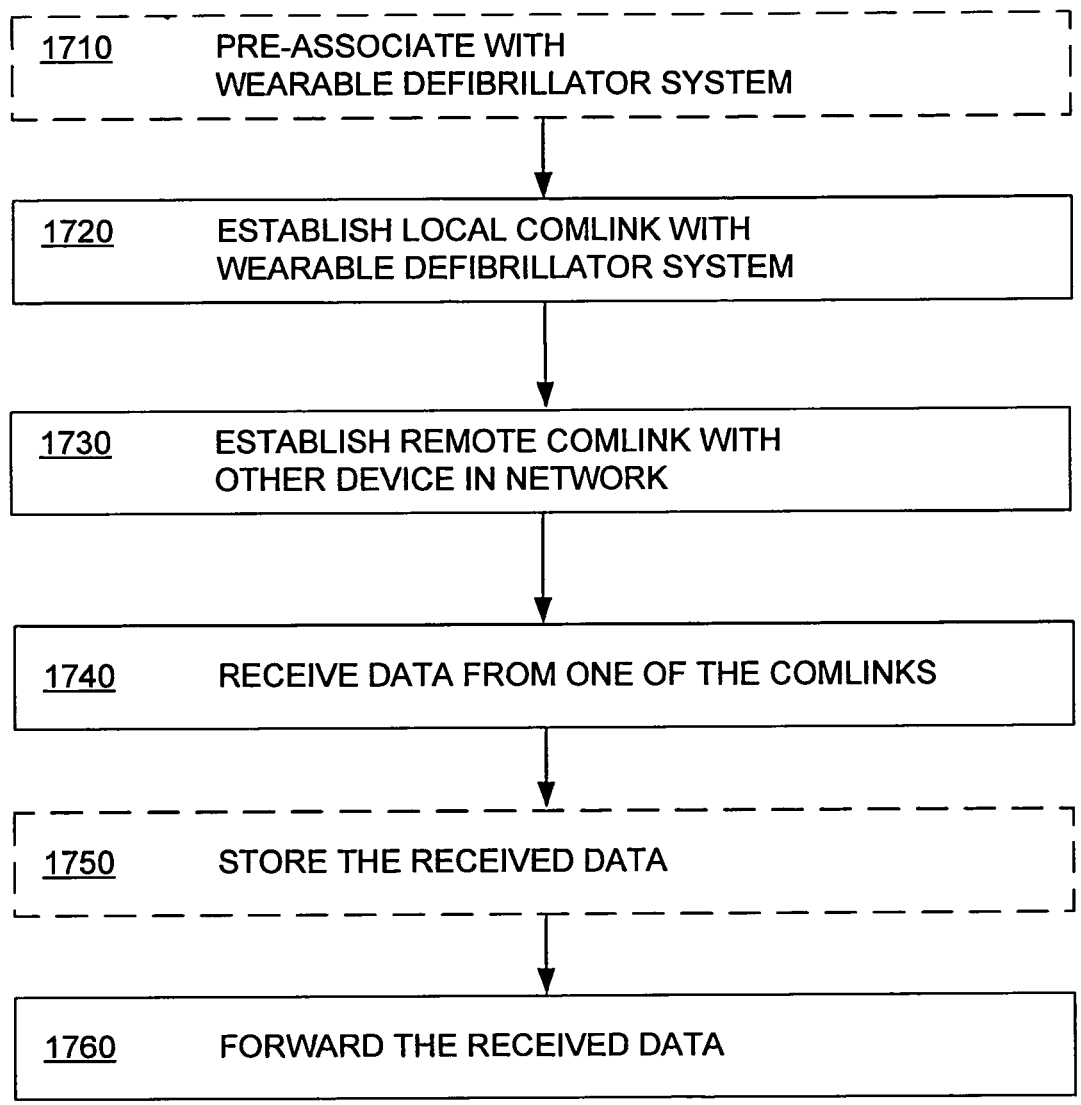
FIG. 17 is a flowchart for illustrating methods for mobile communication devices according to embodiments.

FIG. 17 shows a flowchart 1700 for describing methods according to embodiments. The methods of flowchart 1700 may be practiced by a mobile communication device that can be carried by a user who wears a wearable defibrillation system, such as described above. It will be appreciated that the methods of flowchart 1700 are for mobile communication device 110 to facilitate communication, by acting as an intermediary between wearable communication system 101 and Other Entity 180.

According to an optional operation 1710, the mobile communication device can become associated with the wearable defibrillation system.

Mobile communication device 110 can be an intermediary by receiving data via the one comlink, and forwarding it via the other. Accordingly, in a next operation 1720, a local comlink is established with the defibrillation system. According to another operation 1730, a remote comlink is established with another device in a network. The remote comlink may be established concurrently with the local comlink or not.

According to one more operation 1740, data is received from one of the comlinks, either the local or the remote. According to an optional next operation 1750, the received data is stored for some convenient time, which can exceed 10 sec.

According to a next operation 1760, the received data is forwarded via the remote comlink, to the other device. In some embodiments, the forwarded data is data that has been stored first, according to optional operation 1750. For that, the comlinks need not be established concurrently. In other embodiments, where the comlinks are established concurrently, as data is received from the one of the comlinks, it is forwarded to the other substantially immediately.

Moreover, features and facilities of mobile communication device 110 can be added to the received data for forwarding. For example, the mobile communication device is capable of generating location data about its instant location, such as by having a GPS feature. Accordingly, in one embodiment where forwarding is from the local comlink to the remote comlink, the location data from device 110 is added to the received data, and also forwarded via the remote comlink.

In the flowcharts described above, each operation can be performed as an affirmative step of doing or causing to happen what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention.

This description includes one or more examples, but that does not limit how the invention may be practiced. Indeed, examples or embodiments of the invention may be practiced according to what is described, or yet differently, and also in conjunction with other present or future technologies.

Other embodiments include combinations and sub-combinations of features described herein, including for example, embodiments that are equivalent to: providing or applying a feature in a different order than in a described embodiment, extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A wearable defibrillation system configured to be worn by a patient and to defibrillate the patient, the patient carrying a mobile communication device capable of exchanging data via a remote comlink with one of other devices in a network, the system comprising:
   a support structure configured to be worn by the patient;
   a capacitor coupled to the support structure and configured to store electrical charge for delivering to the patient's body so as to defibrillate the patient; and
   a communication module coupled to the support structure and configured to establish, with the mobile communication device, a local comlink that is distinct from the remote comlink, the communication module further configured to establish, with one of the other devices in the network, a bypass comlink that does not include the mobile communication device and via which data can be transmitted, and
   in which the communication module and the mobile communication device are configured to exchange data via the local comlink.

2. The system of claim 1, in which
   the local comlink uses one of a Bluetooth and a Wi-Fi technology.

3. The system of claim 1, in which
   the mobile communication device includes a user interface for emitting human-perceptible indications, and
   the exchanged data includes guidance data transmitted from the communication module for emitting by the user interface of the mobile communication device as the human-perceptible indications.

4. The system of claim 3, further comprising:
   a processor configured to determine that administering a defibrillation shock is advised, and in which
   the human-perceptible indication is a request to input a report that the patient is alive, and
   the advised shock is not administered if the report is inputted.

5. The system of claim 1, further comprising:
   a certain component; and in which
   the exchanged data includes received control data, and
   an operation of the certain component becomes adjusted responsive to the receipt of the control data.

6. The system of claim 1, further comprising:
   a monitoring device for sensing a local parameter, and
   in which the exchanged data includes the local parameter.

7. The system of claim 6, in which
   the local parameter includes one of a patient physiological parameter, a patient state parameter, a system parameter and an environmental parameter.

8. The system of claim 6, in which
   the local parameter is a physiological parameter chosen from one of the patient's blood perfusion, blood flow, blood pressure, blood oxygen level, pulsatile change in light transmission or reflection properties of perfused tissue, heart sounds, breathing sounds, and pulse.

9. The system of claim 6, in which
   the local parameter is a detected trend in a monitored physiological parameter of the patient.

10. The system of claim 1, in which
    the exchanged data includes patient status data,
    one of a plurality of possible notifying times is selected based on the patient status data, and
    the remote comlink is caused to become established at the selected notifying time.

11. The system of claim 1, in which
    the wearable defibrillation system has been associated with the mobile communication device in advance of establishing the local comlink.

12. The system of claim 1, in which
    the local comlink becomes established if the communication module receives a transaction request from the mobile communication device.

13. The system of claim 12, in which
    the local comlink becomes established if the transaction request additionally meets a validity criterion.

14. The system of claim 12, further comprising:
    a user interface coupled to the support structure and configured to output a human-perceptible indication responsive to receiving the transaction request.

15. The system of claim 14, in which
    the local comlink becomes established if the user interface additionally receives an ack input responsive to outputting the human-perceptible indication.

16. The system of claim 1, in which
    the communication module is configured to attempt to establish the local comlink when a local connection condition is met.

17. The system of claim 16, further comprising:
    a monitoring device configured to sense a local parameter, and
    in which the local connection condition is met if the local parameter exceeds a threshold.

18. The system of claim 16, further comprising:
    a user interface coupled to the support structure for receiving a connection input, and the local connection condition is met if the connection input is received.

19. The system of claim 16, in which
the local connection condition is met if a transaction request is received from the mobile communication device.

20. The system of claim 16, in which
attempting to establish the local comlink includes transmitting a polling signal, and
the local comlink is established additionally if an acceptance signal is received responsive to transmitting the polling signal.

21. The system of claim 16, further comprising:
a user interface coupled to the support structure, and
in which the user interface outputs a human-perceptible indication if the attempt to establish the local comlink fails.

22. The system of claim 1, in which
the communication module is further configured to cause the remote comlink to be established automatically with one of the other devices in the network.

23. The system of claim 1, in which
the communication module is further configured to disestablish automatically the local comlink.

24. The system of claim 1, further comprising:
a user interface coupled to the support structure for receiving a disconnection input, and
in which the local comlink becomes disestablished responsive to receiving the disconnection input.

25. The system of claim 1, further comprising:
a monitoring device for sensing a local parameter, and
in which the local parameter is transmitted via the bypass comlink.

26. The system of claim 1, further comprising:
a certain component; and in which
control data is received via the bypass comlink, and
an operation of the certain component becomes adjusted responsive to the receipt of the control data.

27. The system of claim 1, in which
the bypass comlink becomes established if the communication module attempts to establish the local comlink but the attempt fails.

28. The system of claim 1, further comprising:
a user interface coupled to the support structure for receiving a choice input, and
in which data can be transmitted via one of the local comlink and the bypass comlink instead of the other responsive to the choice input.

29. The system of claim 1, in which
the exchanged data includes patient status data,
one of a plurality of possible notifying times is selected based on the patient status data, and
the bypass comlink is caused to become established at the selected notifying time.

30. A method for a patient, comprising:
wearing a wearable defibrillation system;
carrying a mobile communication device that is capable of exchanging data via a remote comlink with one of other devices in a network, the wearable defibrillation system having an established local comlink with the mobile communication device and exchanging data via the local comlink, the local comlink distinct from the remote comlink, in which the wearable defibrillation system establishes, with one of the other devices in the network, a bypass comlink that does not include the mobile communication device;
entering a choice input so as to establish preferentially one of the local comlink and the bypass comlink over the other; and
receiving a defibrillation shock from the wearable defibrillation system while wearing it.

31. The method of claim 30, in which
the local comlink uses one of a Bluetooth and a Wi-Fi technology.

32. The method of claim 30, further comprising:
causing the mobile communication device to establish the remote comlink.

33. The method of claim 32, in which
causing the remote comlink to become established is performed by entering a remote access request in the mobile communication device.

34. The method of claim 30, further comprising:
perceiving a human-perceptible indication from the mobile communication device, which results from guidance data that has been transmitted via the local comlink; and
acting according to the indication.

35. The method of claim 34, in which
the human-perceptible indication is a challenge to the patient, to perform an indicated act so as to prove they are not suffering from Sudden Cardiac Arrest, and
acting includes performing the indicated act.

36. The method of claim 34, in which
the human-perceptible indication is a request to the patient's reduce body motion so as to improve readings, and
acting includes reducing an amount of body motion.

37. The method of claim 34, in which
the human-perceptible indication is a request to establish the remote comlink, and
acting includes causing the mobile communication device to establish the remote comlink.

38. The method of claim 34, further comprising:
entering, in the mobile communication device, a selection of a preferred one of a plurality of available languages, and
in which the human-perceptible indication is perceived in the preferred language responsive to the entered selection.

39. The method of claim 30, further comprising:
entering a disconnection input to disestablish the local comlink.

* * * * *